(12) United States Patent
Galley et al.

(10) Patent No.: US 7,060,698 B2
(45) Date of Patent: Jun. 13, 2006

(54) BENZOXAZEPINONE DERIVATIVES

(75) Inventors: Guido Galley, Rheinfelden (DE); Robert Alan Goodnow, Jr., Gillette, NJ (US); Jens-Uwe Peters, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 42 days.

(21) Appl. No.: 10/838,054

(22) Filed: May 3, 2004

(65) Prior Publication Data

US 2004/0235819 A1    Nov. 25, 2004

(30) Foreign Application Priority Data

May 19, 2003   (EP) .................................. 03011040

(51) Int. Cl.
*C07D 267/14* (2006.01)
*A61K 31/55* (2006.01)

(52) U.S. Cl. ................... 514/211.05; 540/490
(58) Field of Classification Search ............... 540/490; 514/211.05
See application file for complete search history.

(56) References Cited

FOREIGN PATENT DOCUMENTS

WO   WO 01/98282 A1   12/2001
WO   WO 02/30912 A1   4/2002

OTHER PUBLICATIONS

Sisodia, S. S., et al., Nature Reviews Neuroscience vol. 3, Apr. 2002, pp. 281-290.
Wolfe, M. S., Current Topics in Medicinal Chemistry, 2002, vol. 2 pp. 371-383.
Tsai, J. Y. et al., Current Medicinal Chemistry, 2002, vol. 9, No. 11 pp. 1087-1106.
Sambamurti, K. et al., Drug Development Research, vol. 56, 2002, pp. 211-227.
May, P. C., Drug Discovery Today, vol. 6, No. 9, May, 2001, pp. 459-462.
Nunan, J. et al., FEBS Letters, vol. 483, 2000, pp. 6-10.
Hardy, J. et al., Science, vol. 297, Jul., 2002, pp. 353-356.
Wolfe, M. S., Journal of Medicinal Chemistry, vol. 44 No. 13, 2001, pp. 2039-2060.
Zhang, J. et al, J. Org. Chem. 1999, vol. 64, pp. 1074-1076.
Li, Y. M. et al., PNAS, vol. 97(11), 2000, pp. 6138-6143.
Brockhaus, M. et al., Neuroreport vol. 9(7), 1998, pp. 1481-1486.

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to benzoxazepinone derivatives of formula

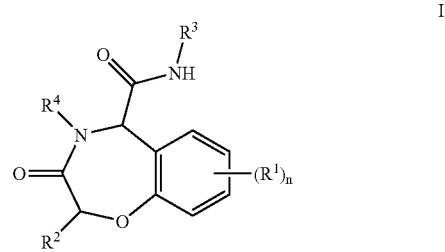

wherein
$R^1$, $R^2$, $R^3$, $R^4$, and n are as defined in the specification and to a pharmaceutically suitable acid addition salt thereof. These compounds are good γ-secretase inhibitors for the treatment of Alzheimer's disease.

37 Claims, No Drawings

BENZOXAZEPINONE DERIVATIVES

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The γ-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis or AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:

Nature Reviews/Neuroscience, Vol. 3, April 2002/281,
Biochemical Society Transactions (2002), Vol. 30. part 4,
Current Topics in Medicinal Chemistry, 2002, 2, 371–383,
Current Medicinal Chemistry, 2002, Vol. 9, No. 11, 1087–1106,
Drug Development Research, 56, 211–227, 2002,
Drug Discovery Today, Vol. 6, No. 9, May 2001, 459–462,
FEBS Letters, 483, (2000), 6–10,
Science, Vol. 297, 353–356, July 2002 and
Journ. of Medicinal Chemistry, Vol. 44, No. 13, 2001, 2039–2060.

SUMMARY OF THE INVENTION

The present invention relates to benzoxazepinone derivatives of formula

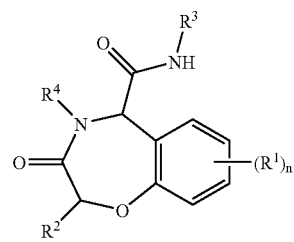

wherein
$R^1$ is hydrogen, lower alkoxy, halogen or —NR'R";
n is 1 or 2;
R',R" are each independently hydrogen or lower alkyl;
$R^2$ is hydrogen, lower alkyl, —$(CH_2)_m$-cycloalkyl, —$(CH_2)_m$-phenyl or —$(CH_2)_m$—O-lower alkyl;
m is 0, 1 or 2;
$R^3$ is lower alkyl, —$(CH_2)_m$—C(O)O-lower alkyl, cycloalkyl or —$(CH_2)_m$-phenyl, which is unsubstituted or substituted by one or two substituents, selected from the group consisting of halogen or lower alkyl;
$R^4$ is —$(CH_2)_o$-phenyl, which is unsubstituted or substituted by one or two substituents, selected from the group consisting of halogen, trifluoromethyl, —NR'R", nitro and —$SO_2NH_2$; or is
cycloalkyl, unsubstituted or substituted by phenyl; or is
—$(CR'R")_o$-heterocyclyl, selected from the group consisting of tetrahydropyran-4-yl, pyridin-3-yl, indol-3-yl optionally substituted by halogen or lower alkoxy; thiophen-2-yl, furan-2-yl, —NH-pyridin-2-yl optionally substituted by nitro; benzoimidazol-2-yl, 2-oxo-tetrahydrofuran, 1-benzyl-piperidin-4-yl, and benzo[1,3]dioxol-5-yl; or is
tetrahydro-naphthalen-1-yl;
—CHR'-naphthalen-2-yl;
fluoren-9-yl;
—$(CH_2)_o$—S-lower alkyl;
—$(CH_2)_o$—S-benzyl;
—$(CH_2)_o$—C(O)NH_2$;
—$(CH_2)_o$NR'R";
—CH[C(O)NH_2]—$(CH_2)_o$-phenyl;
—$(CH_2)_o$—CF_3$; or
—$(CH_2)_o$—CR'R"—CH_2$—NR'R";
and o is 1 or 2;

or a pharmaceutically suitable acid addition salt thereof.

The invention also provides for all forms of optically pure enantiomers, racemates or diastereomeric mixtures for compounds of formulas I. In addition, the invention also provides pharmaceutical compositions which comprise compounds of the invention and a pharmaceutically acceptable carrier.

It has been found that the compounds of the invention are γ-secretase inhibitors and may be useful in the treatment of Alzheimer's disease. Thus, the compounds of this invention will be useful for treating AD by blocking the activity of γ-secretase and reducing or preventing the formation of the various amyloidogenic Abeta peptides. The invention further provides for the treatment of diseases, related to the γ-secretase inhibition, including use of the compounds of the invention for the control or prevention of Alzheimer's disease.

DETAILED DESCRIPTION OF THE INVENTION

The present invention relates to benzoxazepinone derivatives of formula

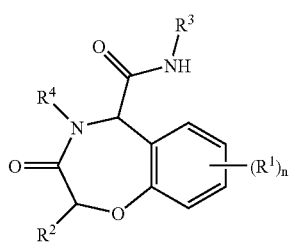

I wherein
$R^1$ is hydrogen, lower alkoxy, halogen or —NR'R";
n is 1 or 2;
R',R" are each independently hydrogen or lower alkyl;
$R^2$ is hydrogen, lower alkyl, —$(CH_2)_m$-cycloalkyl, —$(CH_2)_m$-phenyl or —$(CH_2)_m$—O-lower alkyl;
m is 0, 1 or 2;
$R^3$ is lower alkyl, —$(CH_2)_m$—C(O)O-lower alkyl, cycloalkyl or —$(CH_2)_m$-phenyl, which is unsubstituted or substituted by one or two substituents, selected from the group consisting of halogen or lower alkyl;
$R^4$ is —$(CH_2)_o$-phenyl, which is unsubstituted or substituted by one or two substituents, selected from the group consisting of halogen, trifluoromethyl, —NR'R", nitro and —$SO_2NH_2$; or is
-cycloalkyl, unsubstituted or substituted by phenyl; or is —(CR'R")$_o$-heterocyclyl, selected from the group consisting of tetrahydropyran-4-yl, pyridin-3-yl, indol-3-yl optionally substituted by halogen or lower alkoxy; thiophen-2-yl, furan-2-yl, —NH-pyridin-2-yl optionally substituted by nitro; benzoimidazol-2-yl, 2-oxo-tetrahydrofuran, 1-benzyl-piperidin-4-yl, and benzo[1,3]dioxol-5-yl; or is
tetrahydro-naphthalen-1-yl;
—CHR'-naphthalen-2-yl;
fluoren-9-yl;
—$(CH_2)_o$—S-lower alkyl;
—$(CH_2)_o$—S-benzyl;
—$(CH_2)_o$—C(O)NH$_2$;
—$(CH_2)_o$NR'R";
—CH[C(O)NH$_2$]—$(CH_2)_o$-phenyl;
—$(CH_2)_m$—CF$_3$; or
—$(CH_2)_o$—CR'R"—CH$_2$—NR'R";
and o is 1 or 2;
or a pharmaceutically suitable acid addition salt thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group, containing 3–7 carbon atoms.

The term "halogen" denotes chlorine, iodine, fluorine and bromine.

The term "lower alkoxy" denotes an alkyl group wherein the alkyl residue is as defined above, and which is attached via an oxygen atom.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or, ameliorate symptoms of disease or prolong the survival of the subject being treated.

The most preferred compounds are those, wherein $R^2$ is lower alkyl.

Especially preferred are compounds of this group, wherein $R^3$ is cycloalkyl and $R^4$ is —$(CH_2)_o$-phenyl, substituted by di-halogen or —NR'R", or is tetrahydro-pyran-4-yl, or is -tetrahydro-naphthalen-1-yl or is —$(CH_2)_o$-pyridin-3-yl.

The following specific compounds relate to these groups:
7-Bromo-4-(2,6-difluoro-benzyl)-2-isopropyl-3-oxo-2,3,4,5-tetrahydro-benzo[f][1,4]oxazepine-5-carboxylic acid cyclohexylamide,
7-chloro-4-(4-chloro-2-fluoro-benzyl)-2-isopropyl-3-oxo-2,3,4,5-tetrahydro-benzo[f][1,4]oxazepine-5-carboxylic acid cyclohexylamide,
7-bromo-4-(4-chloro-2-fluoro-benzyl)-2-isopropyl-3-oxo-2,3,4,5-tetrahydro-benzo[f][1,4]oxazepine-5-carboxylic acid cyclohexylamide and
7-bromo-4-(4-dimethylamino-benzyl)-2-isopropyl-9-methoxy-3-oxo-2,3,4,5-tetrahydro-benzo[f][1,4]oxazepine-5-carboxylic acid cyclohexylamide, or
7-chloro-2-ethyl-3-oxo-4-(tetrahydro-pyran-4-yl)-2,3,4,5-tetrahydro-benzo[f][1,4]oxazepine-5-carboxylic acid cyclohexylamide, or
7-chloro-2-isopropyl-3-oxo-4-(1,2,3,4-tetrahydro-naphtha-len-1-yl)-2,3,4,5-tetrahydro-benzo[f][1,4]oxazepine-5-carboxylic acid cyclohexylamid and
8-diethylamino-2-isopropyl-3-oxo-4-(1,2,3,4-tetrahydro-naphthalen-1-yl)-2,3,4,5-tetrahydro -benzo[f][1,4]oxazepine-5-carboxylic acid cyclohexylamide, or
7-chloro-2-isopropyl-3-oxo-4-pyridin-3-ylmethyl-2,3,4,5-tetrahydro-benzo[f][1,4]oxazepine-5-carboxylic acid cyclohexylamide.

Further preferred are compounds with $R^2$ being lower alkyl, wherein $R^3$ is lower alkyl and $R^4$ is
—$(CH_2)_o$-phenyl, substituted by di-halogen or NR'R", or is
—(CR'R")$_o$-indol-3-yl, substituted by lower alkoxy, or is
-cycloalkyl, or is
—$(CH_2)_o$-benzo[1,3]dioxol-5-yl, or is
1-benzyl-piperidin-4-yl.

The following specific compounds relate to these groups:
7-chloro-4-(2,6-difluoro-benzyl)-2-ethyl-3-oxo-2,3,4,5-tetrahydro-benzo[f][1,4]oxazepine-5-carboxylic acid tert-butylamide,
4-(4-dimethylamino-benzyl)-2-isopropyl-3-oxo-2,3,4,5-tetrahydro-benzo[f][1,4]oxazepine-5-carboxylic acid butylamide,
7-chloro-4-(4-dimethylamino-benzyl)-2-isopropyl-3-oxo-2,3,4,5-tetrahydro-benzo[f][1,4]oxazepine-5-carboxylic acid butylamide, 4-(4-dimethylamino-benzyl)-2-isopropyl-8-methoxy-3-oxo-2,3,4,5-tetrahydro-benzo[f][1,4]oxazepine-5-carboxylic acid butylamide,
7-bromo-4-(4-dimethylamino-benzyl)-2-isopropyl-3-oxo-2,3,4,5-tetrahydro-benzo[f][1,4]oxazepine-5-carboxylic acid tert-butylamide and
9-ethoxy-2-isopropyl-4-[2-(5-methoxy-1H-indol-3-yl)-ethyl]-3-oxo-2,3,4,5-tetrahydro-benzo[f][1,4]oxazepine-5-carboxylic acid tert-butylamide and
7-chloro-4-cyclopentyl-2-ethyl-3-oxo-2,3,4,5-tetrahydro-benzo[f][1,4]oxazepine-5-carboxylic acid tert-butylamide and
4-benzo[1,3]dioxol-5-ylmethyl-8-diethylamino-2-isopropyl-3-oxo-2,3,4,5-tetrahydro-benzo[f][1,4]oxazepine-5-carboxylic acid tert-butylamide and
4-(1-benzyl-piperidin-4-yl)-2-isopropyl-3-oxo-2,3,4,5-tetrahydro-benzo[f][1,4]oxazepine-5-carboxylic acid tert-butylamide.

Preferred are further compounds with $R^2$ being lower alkyl, wherein $R^3$ is —$(CH_2)_m$-phenyl and $R^4$ is cycloalkyl.
The following specific compound relate to this group:
7-chloro-4-cyclohexyl-2-isopropyl-3-oxo-2,3,4,5-tetrahydro-benzo[f][1,4]oxazepine-5-carboxylic acid benzylamide.

Preferred are further compounds with $R^2$ being lower alkyl, wherein $R^3$ is —$(CH_2)_m$—C(O)O-lower alkyl and $R^4$ is —$(CH_2)_o$-phenyl, substituted by $CF_3$ or halogen.
The following specific compounds relate to these groups:
{[7-chloro-2-isopropyl-3-oxo-4-(3-trifluoromethyl-benzyl)-2,3,4,5-tetrahydro-benzo[f][1,4]oxazepine-5-carbonyl]-amino}-acetic acid tert-butyl ester and
{[7-bromo-4-(2-chloro-benzyl)-2-isopropyl-9-methoxy-3-oxo-2,3,4,5-tetrahydro-benzo[f][1,4]oxazepine-5-carbonyl]-amino}-acetic acid tert-butyl ester.

In another embodiment, preferred compounds are those wherein $R^3$ is lower alkyl or cycloalkyl. Other preferred compounds are those wherein R is —$(CH_2)_m$-phenyl which is unsubstituted or substituted by one or two substituents selected from the group consisting of halogen or lower alkyl. Yet other preferred compounds as those wherein $R^3$ is —$(CH_2)_m$—C(O)O-lower alkyl.

In a further embodiment, preferred compounds are those wherein $R^4$ is —$(CH_2)_o$-phenyl which is unsubstituted or substituted by one or two substituents selected from the group consisting of halogen, trifluoromethyl, NR'R", nitro or $SO_2NH_2$. Other preferred compounds are those wherein $R^4$ is cycloalkyl which is unsubstituted or substituted by phenyl. Yet other preferred compounds are those wherein $R^4$ is CR'R"-heterocycle selected from the group consisting of tetrahydropyran-4-yl, pyridin-3-yl, indol-3-yl optionally substituted by halogen or lower alkoxy, thiophen-2-yl, furan-2-yl, —NH-pyridin-2-yl optionally substituted by nitro, benzoimidazol-2-yl, 2-oxo-tetrahydrofuran, 1-benzyl-piperidin-4-yl, and benzo[1,3]dioxol-5-yl.

The present compounds of formulas I and their pharmaceutically acceptable salts can be prepared by methods known in the art, for example, by processes described below, which processes comprise
a) reacting a compound of formula

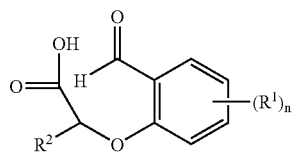

II with a compound of formula $R^4$—$NH_2$    III and with a compound of formula $R^3NC$    IV to produce a compound of formula

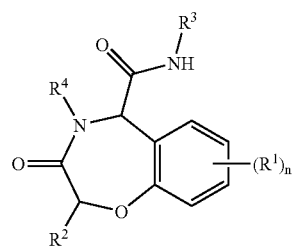

I and if desired, converting the compounds obtained into pharmaceutically acceptable acid addition salts.

The compounds of formula I may be prepared in accordance with the following scheme 1:

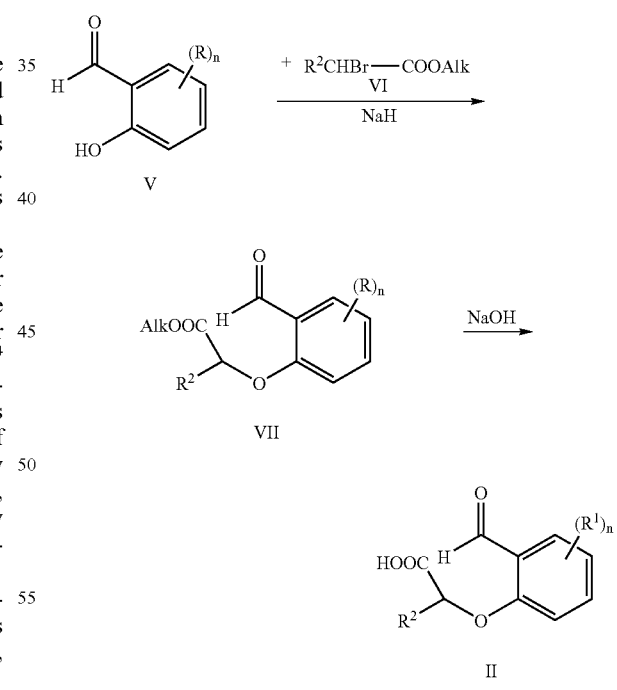

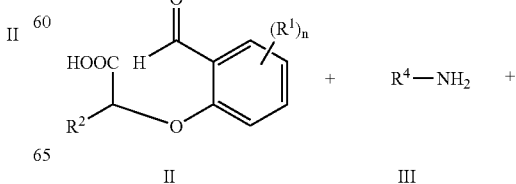

-continued

In this scheme R¹ to R⁴ are as described above.

A general synthesis of the benzoxazepinone skeleton is described in Zhang et al.: J. Org. Chem. 1999, 64, 1074 ff. The corresponding o-hydroxybenzaldehyde (V) is reacted with the alpha-bromocarboxylic acid alkylester (VI) to the 2-formylphenoxyacetic acid alkylester (VII), which is subsequently saponified to the 2-formylphenoxyacetic acid (II). This acid is reacted with the amine (III) and isonitrile (IV) in an Ugi-type reaction to the benzoxazepinone derivative of formula I.

The starting materials of formulas III and IV, and the hydroxybenzaldehyde of formula V and the α-bromoesters of formula VI are commercial available or maybe prepared in accordance with known methods.

The detailed description can be found below and in Examples 1–196.

Some compounds of formula I may be converted to a corresponding acid addition salt, for example compounds containing an amine group. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formulas I and their pharmaceutically usable addition salts possess valuable pharmacological properties. Specifically, it has been found that the compounds of the present invention may inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6× Histidin tail for purification which is expressed in E. coli in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138–6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481–1486 (1998). The preferred compounds show a $IC_{50}$~1.0. In the list below are described some data to the γ-secretase inhibition:

| Example No. | $IC_{50}$ in vitro | Example No. | $IC_{50}$ in vitro |
| --- | --- | --- | --- |
| 1 | 0.28 | 115 | 0.97 |
| 10 | 0.97 | 117 | 0.89 |
| 12 | 1.05 | 122 | 0.96 |
| 16 | 0.89 | 133 | 0.31 |
| 30 | 1.10 | 134 | 0.18 |
| 36 | 0.77 | 150 | 0.67 |
| 76 | 1.16 | 160 | 0.46 |
| 86 | 0.83 | 165 | 0.88 |
| 89 | 1.04 | 178 | 0.81 |
| 96 | 0.62 | 186 | 0.52 |

The present invention also provides pharmaceutical compositions containing compounds of the invention, or pharmaceutically acceptable salts thereof, and a pharmaceutically acceptable carrier. Such pharmaceutical compositions can be in the form of tablets, coated tablets, dragées, hard and soft gelatine capsules, solutions, emulsions or suspensions. The pharmaceutical compositions can also be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like.

Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

Compounds of the present invention as well as their pharmaceutically acceptable salts are inhibitors of γ-secretase. Therefore, the present invention also provides methods of treating or preventing diseases that are mediated by γ-secretase, such as of Alzheimer's disease. Such methods include administering a therapeutically effective amount of a compound of the invention, for example, a compound of formula I, or a pharmaceutically acceptable salt thereof, to an individual in need of such treatment. In one embodiment, the invention provides a method for the treatment or prevention of Alzheimer's disease by administering to an individual a therapeutically effective amount of a compound of formula I.

The compounds and compositions of the present invention can be administered in a conventional manner, for example, orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The dosage at which the compound of the invention is administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. The examples are compounds which can exist in the form of diastereomeric mixtures, as racemates, or as optically pure compounds.

EXAMPLE 1

7-Bromo-4-(2,6-difluoro-benzyl)-2-isopropyl-3-oxo-2,3,4,5-tetrahydro-benzo[f][1,4]oxazepine-5-carboxylic acid cyclohexylamide a) 2-(4-Bromo-2-formyl-phenoxy)-3-methyl-butyric acid To a solution of 0.67 g (3.3 mmol) 5-bromosalicylaldehyde in dimethylformamide (6 ml) 0.2 g sodium hydride (60% suspension in mineral oil, 5 mmol) was added in small portions at 0° C. After stirring for about half an hour 1.05 g ethyl 2-bromo-3-methyl butyrat (5 mmol) was added slowly at room temperature and the mixture was allowed to stir at 90° C. overnight. After cooling ice water (25 ml) and 1N sodium hydroxide solution was added until basic pH. The mixture was extracted three times with ethyl acetate, the combined organic layers were dried (MgSO$_4$) and evaporated. Short column filtration of the residue yielded the ester that was used for the next step without characterization.

The ester was dissolved in 2 ml of methanol and 2N aqueous sodium hydroxide solution (2 ml) was added. After stirring for 1 hour at room temperature the solvent was removed by rotary evaporation. Water (3 ml) and 4N hydrochloric acid was added until pH=4. The mixture was extracted three times with ethyl acetate, the combined organic layers were dried (MgSO$_4$) and evaporated to yield 0.125 g of the title compound as colorless oil.

MS m/e (%): 299.0 (M−H$^+$, 93); 301.0 (M−H$^+$, 100).

b) 7-Bromo-4-(2,6-difluoro-benzyl)-2-isopropyl-3-oxo-2,3,4,5-tetrahydro-benzo[f][1,4]oxazepine-5-carboxylic acid cyclohexylamide To a solution of 0.12 g 2-(4-bromo-2-formyl-phenoxy)-3-methyl-butyric acid (0.4 mmol) in dimethylsulfoxide (0.8 ml) 0.057 g 2,6-difluorobenzylamine (0.4 mmol) and 0.044 g cyclohexyl isocyanide (0.4 mmol) was added and the mixture was allowed to stir overnight. A 10% aqueous sodium chloride solution (5 ml) was added and the mixture was extracted three times with ethyl acetate. The combined organic layers were dried (MgSO$_4$) and evaporated in vacuo. The residue was purified using column chromatography with ethylacetate/hexane (1:4) as eluent to yield 0.03 g of the title compound as light yellow foam.

MS m/e (%): 535.3 (M+H$^+$, 100); 537.3 (M+H$^+$, 95).

EXAMPLE 2

7-Bromo-4-(2,6-difluoro-benzyl)-2-isopropyl-3-oxo-2,3,4,5-tetrahydro-benzo[f][1,4]oxazepine-5-carboxylic acid 3,4-dichloro-benzylamide The title compound was obtained in comparable yields according to the procedures described for example 1 using 1,2-dichloro-4-isocyanomethyl-benzene instead of cyclohexyl isocyanide in step b).

MS m/e (%): 629 (M+H$_2$O+H$^+$, 58); 630 (M+H$_2$O+H$^+$, 100);.

EXAMPLE 3

7-Bromo-4-(2,6-difluoro-benzyl)-2-ethyl-3-oxo-2,3,4,5-tetrahydro-benzo[f][1,4]oxazepine-5-carboxylic acid cyclohexylamide 2,6-Difluorobenzylamine (51 mg, 0.35 mmol) and cyclohexylisocyanide (39 mg, 0.36 mmol) were added to a solution of 2-(4-bromo-2-formyl-phenoxy)-butyric acid (prepared in analogy to 2-(4-bromo-2-formyl-phenoxy)-3-methyl-butyric acid [example 1] from ethyl 2-bromo-3-methyl butyrat, 100 mg, 0.35 mmol) in methanol (0.5 ml). After stirring for 2 h at r.t., the title compound was isolated (diastereomer 1 [inhibitorially active], retention time 2.09 min: 17.9 mg; diastereomer 2 [inhibitorially active], retention time 2.28 min, 7.3 mg, combined yield 14%, MS: m/e=521.1 [M+H$^+$]) from the reaction mixture by reversed-phase, preparative HPLC (YMC CombiPrep C18 column

EXAMPLE 4

7-Bromo-2-cyclohexylmethyl-4-(2,6-difluoro-benzyl)-3-oxo-2,3,4,5-tetrahydro-benzo[f][1,4]oxazepine-5-carboxylic acid cyclohexylamide The title compound, MS: m/e=589.4 [M+H$^+$], was obtained in analogy to example 3 from 2-(4-bromo-2-formyl-phenoxy)-3-cyclohexyl-propionic acid (prepared in analogy to 2-(4-bromo-2-formyl-phenoxy)-3-methyl-butyric acid [example 1] from 2-bromo-3-cyclohexyl-propionic acid ethyl ester) as a mixture of diastereomers.

EXAMPLE 5

7-Bromo-2-butyl-4-(2,6-difluoro-benzyl)-3-oxo-2,3,4,5-tetrahydro-benzo[f][1,4]oxazepine-5-carboxylic acid cyclohexylamide The title compound, MS: m/e=549.4 [M+H$^+$], was obtained in analogy to example 3 from 2-(4-bromo-2-formyl-phenoxy)-hexanoic acid (prepared in analogy to 2-(4-bromo-2-formyl-phenoxy)-3-methyl-butyric acid [example 1] from methyl 2-bromocaproate) as a mixture of diastereomers.

EXAMPLE 6

7-Chloro-4-cyclohexyl-2-ethyl-3-oxo-2,3,4,5-tetrahydro-benzo[f][1,4]oxazepine-5-carboxylic acid cyclohexylamide The title compound, MS: m/e=433.5 (M+H$^+$), was obtained in analogy to example 3 from cyclohexylamine and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 7

7-Chloro-4-(2-chloro-benzyl)-2-ethyl-3-oxo-2,3,4,5-tetrahydro-benzo[f][1,4]oxazepine-5-carboxylic acid cyclohexylamide The title compound, MS: m/e=475.3 (M+H$^+$), was obtained in analogy to example 3 from 2-chlorobenzylamine and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) two separable diastereomers (both inhibitorily active).

EXAMPLE 8

7-Chloro-4-cyclobutyl-2-ethyl-3-oxo-2,3,4,5-tetrahydro-benzo[f][1,4]oxazepine-5-carboxylic acid cyclohexylamide The title compound, MS: m/e=405.4 (M+H$^+$), was obtained in analogy to example 3 from cyclobutylamine and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as a mixture of diastereomers.

EXAMPLE 9

7-Chloro-4-cyclopentyl-2-ethyl-3-oxo-2,3,4,5-tetrahydro-benzo[f][1,4]oxazepine-5-carboxylic acid cyclohexylamide The title compound, MS: m/e=419.4 (M+H$^+$), was obtained in analogy to example 3 from cyclopentylamine and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 10

7-Chloro-2-ethyl-3-oxo-4-(tetrahydro-pyran-4-yl)-2,3,4,5-tetrahydro-benzo[f][1,4]oxazepine-5-carboxylic acid cyclohexylamide The title compound, MS: m/e=435.4 (M+H$^+$), was obtained in analogy to example 3 from 4-aminotetrahydropyran and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 11

7-Chloro-2-ethyl-3-oxo-4-(3-trifluoromethyl-benzyl)-2,3,4,5-tetrahydro-benzo[f][1,4]oxazepine-5-carboxylic acid cyclohexylamide The title compound, MS: m/e=509.3 (M+H$^+$), was obtained in analogy to example 3 from 3-trifluorobenzylamine and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorially active).

EXAMPLE 12

7-Chloro-4-(2,6-difluoro-benzyl)-2-ethyl-3-oxo-2,3,4,5-tetrahydro-benzo[f][1,4]oxazepine-5-carboxylic acid tert-butylamide The title compound, MS: m/e=451.3 (M+H$^+$), was obtained in analogy to example 3 from 2,6-difluorobenzylamine, tert-butylisocyanide, and 2-(4-chloro-2-formyl-phenoxy)-butyric acid (prepared in analogy to 2-(4-Bromo-2-formyl-phenoxy)-3-methyl-butyric acid [example 1] from ethyl 2-bromo-n-butyrate and 5-chlorosalicylaldehyde) as two separable diastereomers (both inhibitorially active).

EXAMPLE 13

7-Chloro-4-cyclohexyl-2-ethyl-3-oxo-2,3,4,5-tetrahydro-benzo[f][1,4]oxazepine-5-carboxylic acid tert-butylamide The title compound, MS: m/e=407.4 (M+H$^+$), was obtained in analogy to example 3 from cyclohexylamine, (50×20 mm, solvent gradient 5–95% CH$_3$CN in 0.1% TFA (aq) over 6.0 min, λ=230 nm, flow rate 40 ml/min).

tert-Butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 14

7-Chloro-4-(2-chloro-benzyl)-2-ethyl-3-oxo-2,3,4,5-tetrahydro-benzo[f][1,4]oxazepine-5-carboxylic acid tert-butylamide The title compound, MS: m/e=449.3 (M+H$^+$), was obtained in analogy to example 3 from 2-chlorobenzylamine,tert-butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 15

7-Chloro-4-cyclobutyl-2-ethyl-3-oxo-2,3,4,5-tetrahydro-benzo[f][1,4]oxazepine-5-carboxylic acid tert-butylamide The title compound, MS: m/e=379.3 (M+H$^+$), was obtained in analogy to example 3 from cyclobutylamine, tert-Butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde).

EXAMPLE 16

7-Chloro-4-cyclopentyl-2-ethyl-3-oxo-2,3,4,5-tetrahydro-benzo[f][1,4]oxazepine-5-carboxylic acid tert-butylamide The title compound MS: m/e=393.3 (M+H$^+$), was obtained in analogy to example 3 from cyclopentylamine, tert-Butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as two separable diastereomers (both inhibitorily active).

EXAMPLE 17

7-Chloro-2-ethyl-3-oxo-4-(tetrahydro-pyran-4-yl)-2,3,4,5-tetrahydro-benzo[f][1,4]oxazepine-5-carboxylic acid tert-butylamide The title compound, MS: m/e=409.3 (M+H$^+$), was obtained in analogy to example 3 from 4-aminotetrahydropyran, tert-Butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde).

EXAMPLE 18

7-Chloro-2-ethyl-3-oxo-4-(3-trifluoromethyl-benzyl)-2,3,4,5-tetrahydro-benzo[f][1,4]oxazepine-5-carboxylic acid tert-butylamide The title compound, MS: m/e=483.5 (M+H$^+$), was obtained in analogy to example 3 from 3-trifluoromethyl-benzylamine, tert-butylisocyanide, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as a mixture of diastereomers.

EXAMPLE 19

{[7-Chloro-4-(2,6-difluoro-benzyl)-2-ethyl-3-oxo-2,3,4,5-tetrahydro-benzo[f][1,4]oxazepine-5-carbonyl]-amino}-acetic acid tert-butyl ester The title compound, MS: m/e=509.3 (M+H$^+$), was obtained in analogy to example 3 from 2,6-difluorobenzylamine, Isocyano-acetic acid tert-butyl ester, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde).

EXAMPLE 20

[(7-Chloro-4-cyclohexyl-2-ethyl-3-oxo-2,3,4,5-tetrahydro-benzo[f][1,4]oxazepine-5-carbonyl)-amino]-acetic acid tert-butyl ester The title compound MS: m/e=465.3 (M+H$^+$), was obtained in analogy to example 3 from cyclohexylamine, Isocyano-acetic acid tert-butyl ester, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as a mixture of diastereomers.

EXAMPLE 21

[(7-Chloro-4-cyclobutyl-2-ethyl-3-oxo-2,3,4,5-tetrahydro-benzo[f][1,4]oxazepine-5-carbonyl)-amino]-acetic acid tert-butyl ester The title compound, MS: m/e=437.3 (M+H$^+$), was obtained in analogy to example 3 from cyclobutylamine, Isocyano-acetic acid tert-butyl ester, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde) as a mixture of diastereomers.

EXAMPLE 22

[(7-Chloro-4-cyclopentyl-2-ethyl-3-oxo-2,3,4,5-tetrahydro-benzo[f][1,4]oxazepine-5-carbonyl)-amino]-acetic acid tert-butyl ester The title compound, MS: m/e=451.4 (M+H$^+$), was obtained in analogy to example 3 from cyclopentylamine, Isocyano-acetic acid tert-butyl ester, and 2-(4-chloro-2-formyl-phenoxy)-butyric acid (prepared in analogy to 2-(4-bromo-2-formyl-phenoxy)-3-methyl-butyric acid [example 1] from ethyl 2-bromo-n-butyrate and 5-chlorosalicylaldehyde).

EXAMPLE 23

7-Chloro-4-(2,6-difluoro-benzyl)-3-oxo-2,3,4,5-tetrahydro-benzo[f][1,4]oxazepine-5-carboxylic acid cyclohexylamide The title compound, MS m/e: 449.14 (M+1), was obtained in analogy to example 3 from 2,6-difluorobenzylamine, (4-chloro-2-formyl-phenoxy)-acetic acid, and Isocyano-cyclohexane.

EXAMPLE 24

4-(2,6-Difluoro-benzyl)-6,8-dimethoxy-3-oxo-2,3,4,
5-tetrahydro-benzo[f][1,4]oxazepine-5-carboxylic
acid tert-butylamide The title compound, MS m/e: 449.18 (M+1), was obtained in analogy to example 3 from 2,6-difluorobenzylamine, (2-formyl-3,5-dimethoxy-phenoxy)-acetic acid, and 2-Isocyano-2-methyl-propane.

EXAMPLE 25

6,8-Dimethoxy-3-oxo-4-(1,2,3,4-tetrahydro-naphthalen-1-yl)-2,3,4,5-tetrahydro-benzo[f][1,4]oxazepine-5-carboxylic acid cyclohexylamide The title compound, MS m/e: 479.25 (M+1), was obtained in analogy to example 3 from 1,2,3,4-tetrahydro-naphthalen-1-ylamine, (2-formyl-3,5-dimethoxy-phenoxy)-acetic acid, and Isocyano-cyclohexane.

EXAMPLE 26

7-Chloro-4-(4-chloro-2-fluoro-benzyl)-3-oxo-2,3,4,
5-tetrahydro-benzo[f][1,4]oxazepine-5-carboxylic
acid cyclohexylamide The title compound, MS m/e: 465.1 (M+1), was obtained in analogy to example 3 from 4-chloro-2-fluorobenzylamine, (4-chloro-2-formyl-phenoxy)-acetic acid, and isocyano-cyclohexane.

EXAMPLE 27

4-(2,6-Difluoro-benzyl)-2-isopropyl-8-methoxy-3-
oxo-2,3,4,5-tetrahydro-benzo[f][1,4]oxazepine-5-
carboxylic acid tert-butylamide The title compound, MS m/e: 461.2 (M+1), was obtained in analogy to example 3 from 2,6-difluorobenzylamine, 2-(2-formyl-5-methoxy-phenoxy)-3-methyl-butyric acid, and 2-isocyano-2-methyl-propane.

EXAMPLE 28

2-Isopropyl-8-methoxy-3-oxo-4-(3-trifluoromethyl-
benzyl)-2,3,4,5-tetrahydro-benzo[f][1,4]oxazepine-
5-carboxylic acid tert-butylamide The title compound, MS m/e: 493.2 (M+1), was obtained in analogy to example 3 from 3-trifluoromethylbenzylamine, 2-(2-formyl-5-methoxy-phenoxy)-3-methyl-butyric acid, and 2-isocyano-2-methyl-propane.

EXAMPLE 29

4-[2-(5-Fluoro-1H-indol-3-yl)-1-methyl-ethyl]-2-
isopropyl-8-methoxy-3-oxo-2,3,4,5-tetrahydro-
benzo[f][1,4]oxazepine-5-carboxylic acid tert-butylamide The title compound, MS m/e: 510.3 (M+1), was obtained in analogy to example 3 from 2-(5-fluoro-1H-indol-3-yl)-1-methyl-ethylamine, 2-(2-formyl-5-methoxy-phenoxy)-3-methyl-butyric acid, and 2-isocyano-2-methyl-propane.

EXAMPLE 30

4-(4-Dimethylamino-benzyl)-2-isopropyl-3-oxo-2,3,
4,5-tetrahydro-benzo[f][1,4]oxazepine-5-carboxylic
acid butylamide The title compound, MS m/e: 438.3 (M+1), was obtained in analogy to example 3 from 4-dimethylaminobenzylamine, 2-(2-formyl-phenoxy)-3-methyl-butyric acid, and 1-isocyano-butane

EXAMPLE 31

2-Isopropyl-4-[2-(5-nitro-pyridin-2-ylamino)-ethyl]-
3-oxo-2,3,4,5-tetrahydro-benzo[f][1,4]oxazepine-5-
carboxylic acid cyclohexylamide The title compound, MS m/e: 496.2 (M+1), was obtained in analogy to example 3 from 2-(5-nitro-pyridin-2-ylamino)-ethylamine, 2-(2-formyl-phenoxy)-3-methyl-butyric acid, and isocyano-cyclohexane.

EXAMPLE 32

7-Bromo-4-(9H-fluoren-9-yl)-3-oxo-2,3,4,5-tetrahydro-benzo[f][1,4]oxazepine-5-carboxylic acid tert-butylamide The title compound, MS m/e: 505.1 (M+1), was obtained in analogy to example 3 from 9H-fluoren-9-ylamine, (4-bromo-2-formyl-phenoxy)-acetic acid, and 2-isocyano-2-methyl-propane.

EXAMPLE 33

8-Diethylamino-4-(9H-fluoren-9-yl)-2-methyl-3-
oxo-2,3,4,5-tetrahydro-benzo[f][1,4]oxazepine-5-
carboxylic acid tert-butylamide The title compound, MS m/e: 512.3 (M+1), was obtained in analogy to example 3 from 9H-fluoren-9-ylamine, 2-(5-diethylamino-2-formyl-phenoxy)-propionic acid, and 2-isocyano-2-methyl-propane.

EXAMPLE 34

7-Chloro-4-(2,6-difluoro-benzyl)-2-isopropyl-3-oxo-
2,3,4,5-tetrahydro-benzo[f][1,4]oxazepine-5-carboxylic acid tert-butylamide The title compound, MS m/e: 465.2 (M+1), was obtained in analogy to example 3 from 2,6-difluorobenzylamine, 2-(4-chloro-2-formyl-phenoxy)-3-methyl-butyric acid, and 2-isocyano-2-methyl-propane.

EXAMPLE 35

7-Chloro-4-(2,6-difluoro-benzyl)-2-isopropyl-3-oxo-
2,3,4,5-tetrahydro-benzo[f][1,4]oxazepine-5-carboxylic acid cyclohexylamide The title compound, MS m/e: 491.2 (M+1), was obtained in analogy to example 3 from 2,6-difluorobenzylamine, 2-(4-chloro-2-formyl-phenoxy)-3-methyl-butyric acid, and isocyano-cyclohexane.

EXAMPLE 36

7-Chloro-4-(4-dimethylamino-benzyl)-2-isopropyl-3-oxo-2,3,4,5-tetrahydro-benzo[f][1,4]oxazepine-5-carboxylic acid butylamide The title compound, MS m/e: 472.2 (M+1), was obtained in analogy to example 3 from 4-dimethylaminobenzylamine, 2-(4-chloro-2-formyl-phenoxy)-3-methyl-butyric acid, and 1-isocyano-butane.

EXAMPLE 37

7-Chloro-2-isopropyl-4-(2-methylsulfanyl-ethyl)-3-oxo-2,3,4,5-tetrahydro-benzo[f][1,4]oxazepine-5-carboxylic acid cyclohexylamide The title compound, MS m/e: 439.2 (M+1), was obtained in analogy to example 3 from 2-methylsulfanyl-ethylamine, 2-(4-chloro-2-formyl-phenoxy)-3-methyl-butyric acid, and isocyano-cyclohexane.

EXAMPLE 38

7-Chloro-4-[2-(1H-indol-3-yl)-ethyl]-2-isopropyl-3-oxo-2,3,4,5-tetrahydro-benzo[f][1,4]oxazepine-5-carboxylic acid tert-butylamide The title compound, MS m/e: 482.2 (M+1), was obtained in analogy to example 3 from 2-(1H-indol-3-yl)-ethylamine, 2-(4-chloro-2-formyl-phenoxy)-3-methyl-butyric acid, and 2-isocyano-2-methyl-propane.

EXAMPLE 39

7,9-Dichloro-4-(2,6-difluoro-benzyl)-2-methyl-3-oxo-2,3,4,5-tetrahydro-benzo[f][1,4]oxazepine-5-carboxylic acid cyclohexylamide The title compound, MS m/e: 497.11 (M+1), was obtained in analogy to example 3 from 2,6-difluorobenzylamine, 2-(2,4-dichloro-6-formyl-phenoxy)-propionic acid, and Isocyano-cyclohexane.

EXAMPLE 40

7-Bromo-4-(2,6-difluoro-benzyl)-2-isopropyl-3-oxo-2,3,4,5-tetrahydro-benzo[f][1,4]oxazepine-5-carboxylic acid tert-butylamide The title compound, MS m/e: 509.12 (M+1), was obtained in analogy to example 3 from 2,6-difluorobenzylamine, 2-(4-bromo-2-formyl-phenoxy)-3-methyl-butyric acid, and 2-isocyano-2-methyl-propane.

EXAMPLE 41

7-Bromo-4-(2-chloro-benzyl)-2-isopropyl-3-oxo-2,3,4,5-tetrahydro-benzo[f][1,4]oxazepine-5-carboxylic acid cyclohexylamide The title compound, MS m/e: 533.2 (M+1), was obtained in analogy to example 3 from 2-chlorobenzylamine, 2-(4-bromo-2-formyl-phenoxy)-3-methyl-butyric acid, and isocyano-cyclohexane.

EXAMPLE 42

4-(4-Chloro-2-fluoro-benzyl)-8-diethylamino-2-isopropyl-3-oxo-2,3,4,5-tetrahydro-benzo[f][1,4]oxazepine-5-carboxylic acid benzylamide The title compound, MS m/e: 552.4 (M+1), was obtained in analogy to example 3 from 4-chloro-2-fluorobenzylamine, 2-(5-diethylamino-2-formyl-phenoxy)-3-methyl-butyric acid, and isocyanomethyl-benzene.

EXAMPLE 43

7-Bromo-4-(2,6-difluoro-benzyl)-2-isopropyl-3-oxo-2,3,4,5-tetrahydro-benzo[f][1,4]oxazepine-5-carboxylic acid butylamide The title compound, MS m/e: 509.1 (M+1), was obtained in analogy to example 3 from 2,6-difluorobenzylamine, 2-(4-bromo-2-formyl-phenoxy)-3-methyl-butyric acid, and 1-isocyano-butane.

EXAMPLE 44

7-Bromo-4-cyclohexyl-2-isopropyl-3-oxo-2,3,4,5-tetrahydro-benzo[f][1,4]oxazepine-5-carboxylic acid tert-butylamide The title compound, MS m/e: 487.2 (M+23), was obtained in analogy to example 3 from cyclohexylamine, 2-(4-bromo-2-formyl-phenoxy)-3-methyl-butyric acid, and 2-isocyano-2-methyl-propane.

EXAMPLE 45

7-Bromo-2-isopropyl-3-oxo-4-(3-trifluoromethyl-benzyl)-2,3,4,5-tetrahydro-benzo[f][1,4]oxazepine-5-carboxylic acid cyclohexylamide The title compound, MS m/e: 567.2 (M+1), was obtained in analogy to example 3 from 3-trifluoromethylbenzylamine, 2-(4-bromo-2-formyl-phenoxy)-3-methyl-butyric acid, and isocyano-cyclohexane.

EXAMPLE 46

4-(1-Benzyl-piperidin-4-yl)-7-bromo-2-isopropyl-3-oxo-2,3,4,5-tetrahydro-benzo[f][1,4]oxazepine-5-carboxylic acid butylamide The title compound, MS m/e: 556.21 (M+1), was obtained in analogy to example 3 from 1-benzyl-piperidin-4-ylamine, 2-(4-bromo-2-formyl-phenoxy)-3-methyl-butyric acid, and 1-isocyano-butane.

EXAMPLE 47

7,9-Dichloro-2-methyl-3-oxo-4-(1,2,3,4-tetrahydro-naphthalen-1-yl)-2,3,4,5-tetrahydro-benzo[f][1,4]oxazepine-5-carboxylic acid tert-butylamide The title compound, MS m/e: 497.15 (M+23), was obtained in analogy to example 3 from 1,2,3,4-tetrahydro-naphthalen-1-ylamine, 2-(2,4-dichloro-6-formyl-phenoxy)-propionic acid, and 2-isocyano-2-methyl-propane.

EXAMPLE 48

7-Bromo-2-isopropyl-3-oxo-4-(1,2,3,4-tetrahydro-naphthalen-1-yl)-2,3,4,5-tetrahydro-benzo[f][1,4]oxazepine-5-carboxylic acid tert-butylamide The title compound, MS m/e: 535.17 (M+23), was obtained in analogy to example 3 from 1,2,3,4-tetrahydro-naphthalen-1-ylamine, 2-(4-bromo-2-formyl-phenoxy)-3-methyl-butyric acid, and 2-isocyano-2-methyl-propane.

EXAMPLE 49

7-Bromo-4-(1-carbamoyl-2-phenyl-ethyl)-2-isopropyl-3-oxo-2,3,4,5-tetrahydro-benzo[f][1,4]oxazepine-5-carboxylic acid cyclohexylamide The title compound, MS m/e: 556.17 (M+1), was obtained in analogy to example 3 from 2-amino-3-phenyl-propionamide, 2-(4-bromo-2-formyl-phenoxy)-3-methyl-butyric acid, and isocyano-cyclohexane.

EXAMPLE 50

7-Bromo-2-isopropyl-3-oxo-4-(1,2,3,4-tetrahydro-naphthalen-1-yl)-2,3,4,5-tetrahydro-benzo[f][1,4]oxazepine-5-carboxylic acid butylamide The title compound, MS m/e: 535.17 (M+23), was obtained in analogy to example 3 from 1,2,3,4-tetrahydro-naphthalen-1-ylamine, 2-(4-bromo-2-formyl-phenoxy)-3-methyl-butyric acid, and 1-isocyano-butane.

EXAMPLE 51

7-Bromo-2-isopropyl-3-oxo-4-pyridin-3-ylmethyl-2,3,4,5-tetrahydro-benzo[f][1,4]oxazepine-5-carboxylic acid tert-butylamide The title compound, MS m/e: 474.13 (M+1), was obtained in analogy to example 3 from pyridin-3-yl-methylamine, 2-(4-bromo-2-formyl-phenoxy)-3-methyl-butyric acid, and 2-isocyano-2-methyl-propane.

EXAMPLE 52

7-Bromo-2-isopropyl-3-oxo-4-pyridin-3-ylmethyl-2,3,4,5-tetrahydro-benzo[f][1,4]oxazepine-5-carboxylic acid cyclohexylamide The title compound, MS m/e: 500.15 (M+1), was obtained in analogy to example 3 from pyridin-3-yl-methylamine, 2-(4-bromo-2-formyl-phenoxy)-3-methyl-butyric acid, and isocyano-cyclohexane.

EXAMPLE 53

7-Bromo-2-isopropyl-3-oxo-4-pyridin-3-ylmethyl-2,3,4,5-tetrahydro-benzo[f][1,4]oxazepine-5-carboxylic acid butylamide The title compound, MS m/e: 474.13 (M+1), was obtained in analogy to example 3 from pyridin-3-yl-methylamine, 2-(4-bromo-2-formyl-phenoxy)-3-methyl-butyric acid, and 1-isocyano-butane.

EXAMPLE 54

7-Bromo-4-[2-(1-indol-3-yl)-ethyl]-2-isopropyl-3-oxo-2,3,4,5-tetrahydro-benzo[f][1,4]oxazepine-5-carboxylic acid tert-butylamide The title compound, MS m/e: 526.16 (M+1), was obtained in analogy to example 3 from 2-(1H-indol-3-yl)-ethylamine, 2-(4-bromo-2-formyl-phenoxy)-3-methyl-butyric acid, and 2-isocyano-2-methyl-propane.

EXAMPLE 55

7-Bromo-2-isopropyl-3-oxo-4-(2,2,2-trifluoro-ethyl)-2,3,4,5-tetrahydro-benzo[f][1,4]oxazepine-5-carboxylic acid cyclohexylamide The title compound, MS m/e: 491.11 (M+1), was obtained in analogy to example 3 from 2,2,2-trifluoroethylamine, 2-(4-bromo-2-formyl-phenoxy)-3-methyl-butyric acid, and isocyano-cyclohexane.

EXAMPLE 56

7-Bromo-4-[2-(1-indol-3-yl)-ethyl]-2-isopropyl-3-oxo-2,3,4,5-tetrahydro-benzo[f][1,4]oxazepine-5-carboxylic acid butylamide The title compound, MS m/e: 526.16 (M+1), was obtained in analogy to example 3 from 2-(1H-indol-3-yl)-ethylamine, 2-(4-bromo-2-formyl-phenoxy)-3-methyl-butyric acid, and 1-isocyano-butane.

EXAMPLE 57

7-Bromo-4-[2-(5-fluoro-1H-indol-3-yl)-1-methyl-ethyl]-2-isopropyl-3-oxo-2,3,4,5-tetrahydro-benzo[f][1,4]oxazepine-5-carboxylic acid tert-butylamide The title compound, MS m/e: 580.2 (M+23), was obtained in analogy to example 3 from 2-(5-fluoro-1H-indol-3-yl)-1-methyl-ethylamine, 2-(4-bromo-2-formyl-phenoxy)-3-methyl-butyric acid, and 2-isocyano-2-methyl-propane.

EXAMPLE 58

4-Cyclohexyl-2-isopropyl-8-methoxy-3-oxo-2,3,4,5-tetrahydro-benzo[f][1,4]oxazepine-5-carboxylic acid tert-butylamide The title compound, MS m/e: 417.27 (M+1), was obtained in analogy to example 3 from cyclohexylamine, 2-(2-formyl-5-methoxy-phenoxy)-3-methyl-butyric acid, and 2-isocyano-2-methyl-propane.

EXAMPLE 59

4-(3,5-Dichloro-benzyl)-2-isopropyl-8-methoxy-3-oxo-2,3,4,5-tetrahydro-benzo[f][1,4]oxazepine-5-carboxylic acid cyclohexylamide The title compound, MS m/e: 541.17 (M+23), was obtained in analogy to example 3 from 3,5-dichlorobenzylamine, 2-(2-formyl-5-methoxy-phenoxy)-3-methyl-butyric acid, and isocyano-cyclohexane.

EXAMPLE 60

4-(2-Chloro-benzyl)-2-isopropyl-8-methoxy-3-oxo-2,3,4,5-tetrahydro-benzo[f][1,4]oxazepine-5-carboxylic acid cyclohexylamide The title compound, MS m/e: 485.22 (M+1), was obtained in analogy to example 3 from 2-chlorobenzylamine, 2-(2-formyl-5-methoxy-phenoxy)-3-methyl-butyric acid, and isocyano-cyclohexane.

EXAMPLE 61

4-(2,6-Difluoro-benzyl)-2-isopropyl-8-methoxy-3-oxo-2,3,4,5-tetrahydro-benzo[f][1,4]oxazepine-5-carboxylic add cyclohexylamide The title compound, MS m/e: 487.23 (M+1), was obtained in analogy to example 3 from 2,6-difluorobenzylamine, 2-(2-formyl-5-methoxy-phenoxy)-3-methyl-butyric acid, and isocyano-cyclohexane.

EXAMPLE 62

2-Isopropyl-8-methoxy-3-oxo-4-(3-trifuoromethyl-benzyl)-2,3,4,5-tetrahydro-benzo[f][1,4]oxazepine-5-carboxylic acid butylamide The title compound, MS m/e: 493.22 (M+1), was obtained in analogy to example 3 from 3-trifluoromethylbenzylamine, 2-(2-formyl-5-methoxy-phenoxy)-3-methyl-butyric acid, and 1-isocyano-butane.

EXAMPLE 63

4-(1-Benzyl-piperidin-4-yl)-2-isopropyl-8-methoxy-3-oxo-2,3,4,5-tetrahydro-benzo[f][1,4]oxazepine-5-carboxylic acid tert-butylamide The title compound, MS m/e: 508.31 (M+1), was obtained in analogy to example 3 from 1-benzyl-piperidin-4-ylamine, 2-(2-formyl-5-methoxy-phenoxy)-3-methyl-butyric acid, and 2-isocyano-2-methyl-propane.

EXAMPLE 64

4-(1-Benzyl-piperidin-4-yl)-2-isopropyl-8-methoxy-3-oxo-2,3,4,5-tetrahydro-benzo[f][1,4]oxazepine-5-carboxylic acid cyclohexylamide The title compound, MS m/e: 534.33 (M+1), was obtained in analogy to example 3 from 1-benzyl-piperidin-4-ylamine, 2-(2-formyl-5-methoxy-phenoxy)-3-methyl-butyric acid, and isocyano-cyclohexane.

EXAMPLE 65

4-(1-Benzyl-piperidin-4-yl)-2-isopropyl-8-methoxy-3-oxo-2,3,4,5-tetrahydro-benzo[f][1,4]oxazepine-5-carboxylic acid butylamide The title compound, MS m/e: 508.31 (M+1), was obtained in analogy to example 3 from 1-benzyl-piperidin-4-ylamine, 2-(2-formyl-5-methoxy-phenoxy)-3-methyl-butyric acid, and 1-isocyano-butane.

EXAMPLE 66

2-Isopropyl-8-methoxy-3-oxo-4-(1,2,3,4-tetrahydro-naphthalen-1-yl)-2,3,4,5-tetrahydro-benzo[f][1,4]oxazepine-5-carboxylic acid tert-butylamide The title compound, MS m/e: 487.27 (M+23), was obtained in analogy to example 3 from 1,2,3,4-tetrahydro-naphthalen-1-ylamine, 2-(2-formyl-5-methoxy-phenoxy)-3-methyl-butyric acid, and 2-isocyano-2-methyl-propane.

EXAMPLE 67

2-Isopropyl-8-methoxy-3-oxo-4-(1,2,3,4-tetrahydro-naphthalen-1-yl)-2,3,4,5-tetrahydro-benzo[f][1,4]oxazepine-5-carboxylic acid cyclohexylamide The title compound, MS m/e: 513.28 (M+23), was obtained in analogy to example 3 from 1,2,3,4-tetrahydro-naphthalen-1-ylamine, 2-(2-formyl-5-methoxy-phenoxy)-3-methyl-butyric acid, and isocyano-cyclohexane.

EXAMPLE 68

2-Isopropyl-8-methoxy-3-oxo-4-(1,2,3,4-tetrahydro-naphthalen-1-yl)-2,3,4,5-tetrahydro-benzo[f][1,4]oxazepine-5-carboxylic acid butylamide The title compound, MS m/e: 465.27 (M+1), was obtained in analogy to example 3 from 1,2,3,4-tetrahydro-naphthalen-1-ylamine, 2-(2-formyl-5-methoxy-phenoxy)-3-methyl-butyric acid, and 1-isocyano-butane.

EXAMPLE 69

2-Isopropyl-8-methoxy-3-oxo-4-pyridin-3-ylmethyl-2,3,4,5-tetrahydro-benzo[f][1,4]oxazepine-5-carboxylic acid tert-butylamide The title compound, MS m/e: 426.23 (M+1), was obtained in analogy to example 3 from pyridin-3-yl-methylamine, 2-(2-formyl-5-methoxy-phenoxy)-3-methyl-butyric acid, and 2-isocyano-2-methyl-propane.

EXAMPLE 70

4-Benzo[1,3]dioxol-5-ylmethyl-2-isopropyl-8-methoxy-3-oxo-2,3,4,5-tetrahydro-benzo[f][1,4]oxazepine-5-carboxylic acid tert-butylamide The title compound, MS m/e: 469.23 (M+1), was obtained in analogy to example 3 from benzo[1,3]dioxol-5-yl-methylamine, 2-(2-formyl-5-methoxy-phenoxy)-3-methyl-butyric acid, and 2-isocyano-2-methyl-propane.

EXAMPLE 71

2-Isopropyl-8-methoxy-3-oxo-4-pyridin-3-ylmethyl-2,3,4,5-tetrahydro-benzo[f][1,4]oxazepine-5-carboxylic acid cyclohexylamide The title compound, MS m/e: 452.25 (M+1), was obtained in analogy to example 3 from pyridin-3-yl-methylamine, 2-(2-formyl-5-methoxy-phenoxy)-3-methyl-butyric acid, and isocyano-cyclohexane.

EXAMPLE 72

4-Benzo[1,3]dioxol-5-ylmethyl-2-isopropyl-8-methoxy-3-oxo-2,3,4,5-tetrahydro-benzo[f][1,4]oxazepine-5-carboxylic acid cyclohexylamide The title compound, MS m/e: 495.24 (M+1), was obtained in analogy to example 3 from benzo[1,3]dioxol-5-yl-methylamine, 2-(2-formyl-5-methoxy-phenoxy)-3-methyl-butyric acid, and isocyano-cyclohexane.

EXAMPLE 73

4-[2-(1-Indol-3-yl)-ethyl]-2-isopropyl-8-methoxy-3-oxo-2,3,4,5-tetrahydro-benzo[f][1,4]oxazepine-5-carboxylic acid tert-butylamide The title compound, MS m/e: 478.26 (M+1), was obtained in analogy to example 3 from 2-(1-indol-3-yl)-ethylamine, 2-(2-formyl-5-methoxy-phenoxy)-3-methyl-butyric acid, and 2-isocyano-2-methyl-propane.

EXAMPLE 74

4-[2-(1H-Indol-3-yl)-ethyl]-2-isopropyl-8-methoxy-3-oxo-2,3,4,5-tetrahydro-benzo[f][1,4]oxazepine-5-carboxylic acid cyclohexylamide The title compound, MS m/e: 504.28 (M+1), was obtained in analogy to example 3 from 2-(1-indol-3-yl)-ethylamine, 2-(2-formyl-5-methoxy-phenoxy)-3-methyl-butyric acid, and isocyano-cyclohexane.

EXAMPLE 75

4-(2,6-Difluoro-benzyl)-2-isopropyl-3-oxo-2,3,4,5-tetrahydro-benzo[f][1,4]oxazepine-5-carboxylic acid cyclohexylamide The title compound, MS m/e: 457.22 (M+1), was obtained in analogy to example 3 from 2,6-difluorobenzylamine, 2-(2-formyl-phenoxy)-3-methyl-butyric acid, and isocyano-cyclohexane.

EXAMPLE 76

4-(1-Benzyl-piperidin-4-yl)-2-isopropyl-3-oxo-2,3,4,5-tetrahydro-benzo[f][1,4]oxazepine-5-carboxylic acid tert-butylamide The title compound, MS m/e: 478.3 (M+1), was obtained in analogy to example 3 from 1-benzyl-piperidin-4-ylamine, 2-(2-formyl-phenoxy)-3-methyl-butyric acid, and 2-isocyano-2-methyl-propane.

EXAMPLE 77

4-(1-Benzyl-piperidin-4-yl)-2-isopropyl-3-oxo-2,3,4,5-tetrahydro-benzo[f][1,4]oxazepine-5-carboxylic acid cyclohexylamide The title compound, MS m/e: 504.32 (M+1), was obtained in analogy to example 3 from 1-benzyl-piperidin-4-ylamine, 2-(2-formyl-phenoxy)-3-methyl-butyric acid, and isocyano-cyclohexane.

EXAMPLE 78

2-Isopropyl-3-oxo-4-pyridin-3-ylmethyl-2,3,4,5-tetrahydro-benzo[f][1,4]oxazepine-5-carboxylic acid tert-butylamide The title compound, MS m/e: 396.22 (M+1), was obtained in analogy to example 3 from pyridin-3-yl-methylamine, 2-(2-formyl-phenoxy)-3-methyl-butyric acid, and 2-isocyano-2-methyl-propane.

EXAMPLE 79

2-Isopropyl-3-oxo-4-pyridin-3-ylmethyl-2,3,4,5-tetrahydro-benzo[f][1,4]oxazepine-5-carboxylic acid cyclohexylamide The title compound, MS m/e: 422.24 (M+1), was obtained in analogy to example 3 from pyridin-3-yl-methylamine, 2-(2-formyl-phenoxy)-3-methyl-butyric acid, and isocyano-cyclohexane.

EXAMPLE 80

4-(3-Dimethylamino-2,2-dimethyl-propyl)-2-isopropyl-3-oxo-2,3,4,5-tetrahydro-benzo[f][1,4]oxazepine-5-carboxylic acid cyclohexylamide The title compound, MS m/e: 444.32 (M+1), was obtained in analogy to example 3 from 2,2,N',N'-tetramethyl-propane-1,3-diamine, 2-(2-formyl-phenoxy)-3-methyl-butyric acid, and isocyano-cyclohexane.

EXAMPLE 81

4-[2-(1H-Indol-3-yl)-ethyl]-2-isopropyl-3-oxo-2,3,4,5-tetrahydro-benzo[f][1,4]oxazepine-5-carboxylic acid tert-butylamide The title compound, MS m/e: 448.25 (M+1), was obtained in analogy to example 3 from 2-(1H-indol-3-yl)-ethylamine, 2-(2-formyl-phenoxy)-3-methyl-butyric acid, and 2-isocyano-2-methyl-propane.

EXAMPLE 82

4-[2-(1H-Indol-3-yl)-ethyl]-2-isopropyl-3-oxo-2,3,4,5-tetrahydro-benzo[f][1,4]oxazepine-5-carboxylic acid butylamide The title compound, MS m/e: 448.25 (M+1), was obtained in analogy to example 3 from 2-(1H-indol-3-yl)-ethylamine, 2-(2-formyl-phenoxy)-3-methyl-butyric acid, and 1-isocyano-butane.

EXAMPLE 83

2-Isopropyl-4-[2-(5-methoxy-1H-indol-3-yl)-ethyl]-3-oxo-2,3,4,5-tetrahydro-benzo[f][1,4]oxazepine-5-carboxylic acid tert-butylamide The title compound, MS m/e: 478.26 (M+1), was obtained in analogy to example 3 from 2-(5-methoxy-1H-indol-3-yl)-ethylamine, 2-(2-formyl-phenoxy)-3-methyl-butyric acid, and 2-isocyano-2-methyl-propane.

EXAMPLE 84

2-Isopropyl-4-[2-(5-methoxy-1H-indol-3-yl)-ethyl]-3-oxo-2,3,4,5-tetrahydro-benzo[f][1,4]oxazepine-5-carboxylic acid cyclohexylamide The title compound, MS m/e: 504.28 (M+1), was obtained in analogy to example 3 from 2-(5-methoxy-1H-indol-3-yl)-ethylamine, 2-(2-formyl-phenoxy)-3-methyl-butyric acid, and isocyano-cyclohexane.

EXAMPLE 85

7-Chloro-4-(2-chloro-benzyl)-2-isopropyl-3-oxo-2,3,4,5-tetrahydro-benzo[f][1,4]oxazepine-5-carboxylic acid cyclohexylamide The title compound, MS m/e: 489.16 (M+1), was obtained in analogy to example 3 from 2-chlorobenzylamine, 2-(4-chloro-2-formyl-phenoxy)-3-methyl-butyric acid, and isocyano-cyclohexane.

EXAMPLE 86

7-Chloro-2-isopropyl-3-oxo-4-(1,2,3,4-tetrahydro-naphthalen-1-yl)-2,3,4,5-tetrahydro-benzo[f][1,4]oxazepine-5-carboxylic acid cyclohexylamid The title compound, MS m/e: 517.3943 (M+23), was obtained in analogy to example 3 from 1,2,3,4-tetrahydro-naphthalen-1-ylamine, 2-(4-chloro-2-formyl-phenoxy)-3-methyl-butyric acid, and isocyano-cyclohexane.

EXAMPLE 87

4-(2-Benzylsulfanyl-ethyl)-7-chloro-2-isopropyl-3-oxo-2,3,4,5-tetrahydro-benzo[f][1,4]oxazepine-5-carboxylic acid cyclohexylamide The title compound, MS m/e: 537.2 (M+23), was obtained in analogy to example 3 from 2-benzylsulfanyl-ethylamine, 2-(4-chloro-2-formyl-phenoxy)-3-methyl-butyric acid, and isocyano-cyclohexane.

EXAMPLE 88

7-Chloro-2-isopropyl-3-oxo-4-pyridin-3-ylmethyl-2,3,4,5-tetrahydro-benzo[f][1,4]oxazepine-5-carboxylic acid tert-butylamide The title compound, MS m/e: 430.18 (M+1), was obtained in analogy to example 3 from pyridin-3-yl-methylamine, 2-(4-chloro-2-formyl-phenoxy)-3-methyl-butyric acid, and 2-isocyano-2-methyl-propane.

EXAMPLE 89

7-Chloro-2-isopropyl-3-oxo-4-pyridin-3-ylmethyl-2,3,4,5-tetrahydro-benzo[f][1,4]oxazepine-5-carboxylic acid cyclohexylamide The title compound, MS m/e: 456.2 (M+1), was obtained in analogy to example 3 from pyridin-3-yl-methylamine, 2-(4-chloro-2-formyl-phenoxy)-3-methyl-butyric acid, and isocyano-cyclohexane.

EXAMPLE 90

7-Chloro-2-isopropyl-3-oxo-4-pyridin-3-ylmethyl-2,3,4,5-tetrahydro-benzo[f][1,4]oxazepine-5-carboxylic acid butylamide The title compound, MS m/e: 430.18 (M+1), was obtained in analogy to example 3 from pyridin-3-yl-methylamine, 2-(4-chloro-2-formyl-phenoxy)-3-methyl-butyric acid, and 1-isocyano-butane.

EXAMPLE 91

7-Chloro-4-(3-diethylamino-propyl)-2-isopropyl-3-oxo-2,3,4,5-tetrahydro-benzo[f][1,4]oxazepine-5-carboxylic acid cyclohexylamide The title compound, MS m/e: 478.28 (M+1), was obtained in analogy to example 3 from N',N'-diethyl-propane-1,3-diamine, 2-(4-chloro-2-formyl-phenoxy)-3-methyl-butyric acid, and isocyano-cyclohexane.

EXAMPLE 92

7-Chloro-2-isopropyl-4-[2-(5-methoxy-1H-indol-3-yl)-ethyl]-3-oxo-2,3,4,5-tetrahydro-benzo[f][1,4]oxazepine-5-carboxylic acid cyclohexylamide The title compound, MS m/e: 538.24 (M+1), was obtained in analogy to example 3 from 2-(5-methoxy-1H-indol-3-yl)-ethylamine, 2-(4-chloro-2-formyl-phenoxy)-3-methyl-butyric acid, and isocyano-cyclohexane.

EXAMPLE 93

4-(4-Chloro-2-fluoro-benzyl)-7-methoxy-3-oxo-2-phenyl-2,3,4,5-tetrahydro-benzo[f][1,4]oxazepine-5-carboxylic acid tert-butylamide The title compound, MS m/e: 511.17 (M+1), was obtained in analogy to example 3 from 4-chloro-2-fluorobenzylamine, (2-formyl-4-methoxy-phenoxy)-phenyl-acetic acid, and 2-isocyano-2-methyl-propane.

EXAMPLE 94

7-Chloro-4-[2-(1H-indol-3-yl)-ethyl]-2-isopropyl-3-oxo-2,3,4,5-tetrahydro-benzo[f][1,4]oxazepine-5-carboxylic acid butylamide The title compound, MS m/e: 482.21 (M+1), was obtained in analogy to example 3 from 2-(1H-indol-3-yl)-ethylamine, 2-(4-chloro-2-formyl-phenoxy)-3-methyl-butyric acid, and 1-isocyano-butane.

EXAMPLE 95

7-Chloro-2-isopropyl-4-[2-(5-methoxy-1H-indol-3-yl)-ethyl]-3-oxo-2,3,4,5-tetrahydro-benzo[f][1,4]oxazepine-5-carboxylic acid tert-butylamide The title compound, MS m/e: 512.22 (M+1), was obtained in analogy to example 3 from 2-(5-methoxy-1H-indol-3-yl)-ethylamine, 2-(4-chloro-2-formyl-phenoxy)-3-methyl-butyric acid, and 2-isocyano-2-methyl-propane.

EXAMPLE 96

7-Chloro-4-(4-chloro-2-fluoro-benzyl)-2-isopropyl-3-oxo-2,3,4,5-tetrahydro-benzo[f][1,4]oxazepine-5-carboxylic acid cyclohexylamide The title compound, MS m/e: 507.15 (M+1), was obtained in analogy to example 3 from 4-chloro-2-fluorobenzylamine, 2-(4-chloro-2-formyl-phenoxy)-3-methyl-butyric acid, and isocyano-cyclohexane.

EXAMPLE 97

7,9-Dichloro-4-(4-chloro-2-fluoro-benzyl)-2-methyl-3-oxo-2,3,4,5-tetrahydro-benzo[f][1,4]oxazepine-5-carboxylic acid cyclohexylamide The title compound, MS m/e: 513.08 (M+1), was obtained in analogy to example 3 from 4-chloro-2-fluorobenzylamine, 2-(2,4-dichloro-6-formyl-phenoxy)-propionic acid, and isocyano-cyclohexane.

EXAMPLE 98

4-(9H-Fluoren-9-yl)-7-methoxy-2-methyl-3-oxo-2,3,4,5-tetrahydro-benzo[f][1,4]oxazepine-5-carboxylic acid cyclohexylamide The title compound, MS m/e: 497.24 (M+1), was obtained in analogy to example 3 from 9H-fluoren-9-ylamine, 2-(2-formyl-4-methoxy-phenoxy)-propionic acid, and isocyano-cyclohexane.

EXAMPLE 99

4-(3,5-Dichloro-benzyl)-8-diethylamino-2-isopropyl-3-oxo-2,3,4,5-tetrahydro-benzo[f][1,4]oxazepine-5-carboxylic acid tert-butylamide The title compound, MS m/e: 534.22 (M+1), was obtained in analogy to example 3 from 3,5-dichlorobenzylamine, 2-(5-diethylamino-2-formyl-phenoxy)-3-methyl-butyric acid) and 2-isocyano-2-methyl-propane.

EXAMPLE 100

4-(3,5-Dichloro-benzyl)-8-diethylamino-2-isopropyl-3-oxo-2,3,4,5-tetrahydro-benzo[f][1,4]oxazepine-5-carboxylic acid cyclohexylamide The title compound, MS m/e: 560.24 (M+1), was obtained in analogy to example 3 from 3,5-dichlorobenzylamine, 2-(5-diethylamino-2-formyl-phenoxy)-3-methyl-butyric acid, and isocyano-cyclohexane.

EXAMPLE 101

8-Diethylamino-2-isopropyl-3-oxo-4-(3-trifluoromethyl-benzyl)-2,3,4,5-tetrahydro-benzo[f][1,4]oxazepine-5-carboxylic acid cyclohexylamide The title compound, MS m/e: 560.3 (M+1), was obtained in analogy to example 3 from 3-trifluoromethylbenzylamine, 2-(5-diethylamino-2-formyl-phenoxy)-3-methyl-butyric acid, and isocyano-cyclohexane.

EXAMPLE 102

8-Diethylamino-4-[2-(1H-indol-3-yl)-ethyl]-2-isopropyl-3-oxo-2,3,4,5-tetrahydro-benzo[f][1,4]oxazepine-5-carboxylic acid cyclohexylamide The title compound, MS m/e: 545.34 (M+1), was obtained in analogy to example 3 from 2-(1H-indol-3-yl)-ethylamine, 2-(5-diethylamino-2-formyl-phenoxy)-3-methyl-butyric acid, and isocyano-cyclohexane.

EXAMPLE 103

4-(4-Dimethylamino-benzyl)-2-isopropyl-8-methoxy-3-oxo-2,3,4,5-tetrahydro-benzo[f][1,4]oxazepine-5-carboxylic acid cyclohexylamide The title compound, MS m/e: 494.29 (M+1), was obtained in analogy to example 3 from 4-dimethylaminobenzylamine, 2-(2-formyl-5-methoxy-phenoxy)-3-methyl-butyric acid, and isocyano-cyclohexane.

EXAMPLE 104

4-(2-Chloro-benzyl)-8-diethylamino-2-isopropyl-3-oxo-2,3,4,5-tetrahydro-benzo[f][1,4]oxazepine-5-carboxylic acid tert-butylamide The title compound, MS m/e: 500.3 (M+1), was obtained in analogy to example 3 from 2-chlorobenzylamine, 2-(5-diethylamino-2-formyl-phenoxy)-3-methyl-butyric acid, and 2-isocyano-2-methyl-propane.

EXAMPLE 105

8-Diethylamino-4-(2,6-difluoro-benzyl)-2-isopropyl-3-oxo-2,3,4,5-tetrahydro-benzo[f][1,4]oxazepine-5-carboxylic acid tert-butylamide The title compound, MS m/e: 502.3 (M+1), was obtained in analogy to example 3 from 2,6-difluorobenzylamine, 2-(5-diethylamino-2-formyl-phenoxy)-3-methyl-butyric acid, and 2-isocyano-2-methyl-propane.

EXAMPLE 106

4-(2-Chloro-benzyl)-8-diethylamino-2-isopropyl-3-oxo-2,3,4,5-tetrahydro-benzo[f][1,4]oxazepine-5-carboxylic acid cyclohexylamide The title compound, MS m/e: 526.4 (M+1), was obtained in analogy to example 3 from 2-chlorobenzylamine, 2-(5-diethylamino-2-formyl-phenoxy)-3-methyl-butyric acid, and isocyano-cyclohexane.

EXAMPLE 107

8-Diethylamino-4-(2,6-difluoro-benzyl)-2-isopropyl-3-oxo-2,3,4,5-tetrahydro-benzo[f][1,4]oxazepine-5-carboxylic acid cyclohexylamide The title compound, MS m/e: 528.4 (M+1), was obtained in analogy to example 3 from 2,6-difluorobenzylamine, 2-(5-diethylamino-2-formyl-phenoxy)-3-methyl-butyric acid, and isocyano-cyclohexane.

EXAMPLE 108

4-(2-Chloro-benzyl)-8-diethylamino-2-isopropyl-3-oxo-2,3,4,5-tetrahydro-benzo[f][1,4]oxazepine-5-carboxylic acid butylamide The title compound, MS m/e: 500.4 (M+1), was obtained in analogy to example 3 from 2-chlorobenzylamine, 2-(5-diethylamino-2-formyl-phenoxy)-3-methyl-butyric acid, and 1-isocyano-butane.

EXAMPLE 109

8-Diethylamino-4-(2,6-difluoro-benzyl)-2-isopropyl-3-oxo-2,3,4,5-tetrahydro-benzo[f][1,4]oxazepine-5-carboxylic acid butylamide The title compound, MS m/e: 502.4 (M+1), was obtained in analogy to example 3 from 2,6-difluorobenzylamine, 2-(5-diethylamino-2-formyl-phenoxy)-3-methyl-butyric acid, and 1-isocyano-butane.

EXAMPLE 110

4-Cyclohexyl-8-diethylamino-2-isopropyl-3-oxo-2,3,4,5-tetrahydro-benzo[f][1,4]oxazepine-5-carboxylic acid tert-butylamide The title compound, MS m/e: 458.4 (M+1), was obtained in analogy to example 3 from cyclohexylamine, 2-(5-diethylamino-2-formyl-phenoxy)-3-methyl-butyric acid, and 2-isocyano-2-methyl-propane.

EXAMPLE 111

8-Diethylamino-2-isopropyl-3-oxo-4-(3-trifluoromethyl-benzyl)-2,3,4,5-tetrahydro-benzo[f][1,4]oxazepine-5-carboxylic acid tert-butylamide The title compound, MS m/e: 534.4 (M+1), was obtained in analogy to example 3 from 3-trifluoromethylbenzylamine, 2-(5-diethylamino-2-formyl-phenoxy)-3-methyl-butyric acid, and 2-isocyano-2-methyl-propane.

EXAMPLE 112

8-Diethylamino-2-isopropyl-3-oxo-4-(3-trifluoromethyl-benzyl)-2,3,4,5-tetrahydro-benzo[f][1,4]oxazepine-5-carboxylic acid butylamide The title compound, MS m/e: 534.4 (M+1), was obtained in analogy to example 3 from 3-trifluoromethylbenzylamine, 2-(5-diethylamino-2-formyl-phenoxy)-3-methyl-butyric acid, and 1-isocyano-butane.

EXAMPLE 113

4-(1-Benzyl-piperidin-4-yl)-8-diethylamino-2-isopropyl-3-oxo-2,3,4,5-tetrahydro-benzo[f][1,4]oxazepine-5-carboxylic acid tert-butylamide The title compound, MS m/e: 549.4 (M+1), was obtained in analogy to example 3 from 1-benzyl-piperidin-4-ylamine, 2-(5-diethylamino-2-formyl-phenoxy)-3-methyl-butyric acid, and 2-isocyano-2-methyl-propane.

EXAMPLE 114

8-Diethylamino-2-isopropyl-3-oxo-4-(1,2,3,4-tetrahydro-naphthalen-1-yl)-2,3,4,5-tetrahydro-benzo[f][1,4]oxazepine-5-carboxylic acid tert-butylamide The title compound, MS m/e: 506.4 (M+1), was obtained in analogy to example 3 from 1,2,3,4-tetrahydro-naphthalen-1-ylamine, 2-(5-diethylamino-2-formyl-phenoxy)-3-methyl-butyric acid, and 2-isocyano-2-methyl-propane.

EXAMPLE 115

8-Diethylamino-2-isopropyl-3-oxo-4-(1,2,3,4-tetrahydro-naphthalen-1-yl)-2,3,4,5-tetrahydro-benzo[f][1,4]oxazepine-5-carboxylic acid cyclohexylamide The title compound, MS m/e: 532.4 (M+1), was obtained in analogy to example 3 from 1,2,3,4-tetrahydro-naphthalen-1-ylamine, 2-(5-diethylamino-2-formyl-phenoxy)-3-methyl-butyric acid, and isocyano-cyclohexane.

EXAMPLE 116

8-Diethylamino-2-isopropyl-3-oxo-4-(1,2,3,4-tetrahydro-naphthalen-1-yl)-2,3,4,5-tetrahydro-benzo[f][1,4]oxazepine-5-carboxylic acid butylamide The title compound, MS m/e: 506.4 (M+1), was obtained in analogy to example 3 from 1,2,3,4-tetrahydro-naphthalen-1-ylamine, 2-(5-diethylamino-2-formyl-phenoxy)-3-methyl-butyric acid, and 1-isocyano-butane.

EXAMPLE 117

4-Benzo[1,3]dioxol-5-ylmethyl-8-diethylamino-2-isopropyl-3-oxo-2,3,4,5-tetrahydro-benzo[f][1,4]oxazepine-5-carboxylic acid tert-butylamide The title compound, MS m/e: 510.4 (M+1), was obtained in analogy to example 3 from benzo[1,3]dioxol-5-yl-methylamine, 2-(5-diethylamino-2-formyl-phenoxy)-3-methyl-butyric acid, and 2-isocyano-2-methyl-propane.

EXAMPLE 118

4-Benzo[1,3]dioxol-5-ylmethyl-8-diethylamino-2-isopropyl-3-oxo-2,3,4,5-tetrahydro-benzo[f][1,4]oxazepine-5-carboxylic acid cyclohexylamide The title compound, MS m/e: 536.4 (M+1), was obtained in analogy to example 3 from benzo[1,3]dioxol-5-yl-methylamine, 2-(5-diethylamino-2-formyl-phenoxy)-3-methyl-butyric acid, and isocyano-cyclohexane.

EXAMPLE 119

4-Benzo[1,3]dioxol-5-ylmethyl-8-diethylamino-2-isopropyl-3-oxo-2,3,4,5-tetrahydro-benzo[f][1,4]oxazepine-5-carboxylic acid butylamide The title compound, MS m/e: 510.4 (M+1), was obtained in analogy to example 3 from benzo[1,3]dioxol-5-yl-methylamine, 2-(5-diethylamino-2-formyl-phenoxy)-3-methyl-butyric acid, and 1-isocyano-butane.

EXAMPLE 120

8-Diethylamino-4-[2-(1-indol-3-yl)-ethyl]-2-isopropyl-3-oxo-2,3,4,5-tetrahydro-benzo[f][1,4]oxazepine-5-carboxylic acid tert-butylamide The title compound, MS m/e: 519.4 (M+1), was obtained in analogy to example 3 from 2-(1H-indol-3-yl)-ethylamine, 2-(5-diethylamino-2-formyl-phenoxy)-3-methyl-butyric acid, and 2-isocyano-2-methyl-propane.

EXAMPLE 121

8-Diethylamino-2-isopropyl-4-[2-(5-methoxy-1H-indol-3-yl)-ethyl]-3-oxo-2,3,4,5-tetrahydro-benzo[f][1,4]oxazepine-5-carboxylic acid butylamide The title compound, MS m/e: 549.4 (M+1), was obtained in analogy to example 3 from 2-(5-methoxy-1H-indol-3-yl)-ethylamine, 2-(5-diethylamino-2-formyl-phenoxy)-3-methyl-butyric acid, and 1-isocyano-butane.

EXAMPLE 122

4-(4-Dimethylamino-benzyl)-2-isopropyl-8-methoxy-3-oxo-2,3,4,5-tetrahydro-benzo[f][1,4]oxazepine-5-carboxylic acid butylamide The title compound, MS m/e: 468.4 (M+1), was obtained in analogy to example 3 from 4-dimethylaminobenzylamine, 2-(2-formyl-5-methoxy-phenoxy)-3-methyl-butyric acid, and 1-isocyano-butane.

EXAMPLE 123

4-(4-Chloro-2-fluoro-benzyl)-2-isopropyl-8-methoxy-3-oxo-2,3,4,5-tetrahydro-benzo[f][1,4]oxazepine-5-carboxylic acid tert-butylamide The title compound, MS m/e: 477.2 (M+1), was obtained in analogy to example 3 from 4-chloro-2-fluorobenzylamine, 2-(2-formyl-5-methoxy-phenoxy)-3-methyl-butyric acid, and 2-isocyano-2-methyl-propane.

EXAMPLE 124

4-(4-Chloro-2-fluoro-benzyl)-2-isopropyl-8-methoxy-3-oxo-2,3,4,5-tetrahydro-benzo[f][1,4]oxazepine-5-carboxylic acid cyclohexylamide The title compound, MS m/e: 503.3 (M+1), was obtained in analogy to example 3 from 4-chloro-2-fluorobenzylamine, 2-(2-formyl-5-methoxy-phenoxy)-3-methyl-butyric acid, and isocyano-cyclohexane.

EXAMPLE 125

4-(4-Chloro-2-fluoro-benzyl)-2-isopropyl-8-methoxy-3-oxo-2,3,4,5-tetrahydro-benzo[f][1,4]oxazepine-5-carboxylic acid butylamide The title compound, MS m/e: 477.3 (M+1), was obtained in analogy to example 3 from 4-chloro-2-fluorobenzylamine, 2-(2-formyl-5-methoxy-phenoxy)-3-methyl-butyric acid, and 1-isocyano-butane.

EXAMPLE 126

7-Bromo-4-(2,6-difluoro-benzyl)-2-methyl-3-oxo-2,3,4,5-tetrahydro-benzo[f][1,4]oxazepine-5-carboxylic acid cyclohexylamide The title compound, MS m/e: 529.2 (M+23), was obtained in analogy to example 3 from 2,6-difluorobenzylamine, 2-(4-bromo-2-formyl-phenoxy)-propionic acid, and isocyano-cyclohexane.

EXAMPLE 127

{[4-(1-Benzyl-piperidin-4-yl)-2-isopropyl-3-oxo-2,3,4,5-tetrahydro-benzo[f][1,4]oxazepine-5-carbonyl]-amino}-acetic acid tert-butyl ester The title compound, MS m/e: 536.4 (M+1), was obtained in analogy to example 3 from 1-benzyl-piperidin-4-ylamine, 2-(2-formyl-phenoxy)-3-methyl-butyric acid, and isocyanoacetic acid tert-butyl ester.

EXAMPLE 128

({7-Chloro-2-isopropyl-4-[2-(5-methoxy-1H-indol-3-yl)-ethyl]-3-oxo-2,3,4,5-tetrahydro-benzo[f][1,4]oxazepine-5-carbonyl}-amino)-acetic acid tert-butyl ester The title compound, MS m/e: 592.2 (M+23), was obtained in analogy to example 3 from 2-(5-methoxy-1H-indol-3-yl)-ethylamine, 2-(4-chloro-2-formyl-phenoxy)-3-methyl-butyric acid, and isocyano-acetic acid tert-butyl ester.

EXAMPLE 129

({7-Chloro-2-isopropyl-4-[2-(4-nitro-phenyl)-ethyl]-3-oxo-2,3,4,5-tetrahydro-benzo[f][1,4]oxazepine-5-carbonyl}-amino)-acetic acid tert-butyl ester The title compound, MS m/e: 546.2 (M+1), was obtained in analogy to example 3 from 4-nitrophenylethylamine, 2-(4-chloro-2-formyl-phenoxy)-3-methyl-butyric acid, and isocyano-acetic acid tert-butyl ester.

EXAMPLE 130

4-(1H-Benzoimidazol-2-ylmethyl)-9-ethoxy-2-isopropyl-3-oxo-2,3,4,5-tetrahydro-benzo[f][1,4]oxazepine-5-carboxylic acid tert-butylamide The title compound, MS m/e: 479.3 (M+1), was obtained in analogy to example 3 from benzoimidazol-2-yl-methylamine, 2-(2-ethoxy-6-formyl-phenoxy)-3-methyl-butyric acid, and 2-isocyano-2-methyl-propane.

EXAMPLE 131

4-(1H-Benzoimidazol-2-ylmethyl)-9-ethoxy-2-isopropyl-3-oxo-2,3,4,5-tetrahydro-benzo[f][1,4]oxazepine-5-carboxylic acid cyclohexylamide The title compound, MS m/e: 505.3 (M+1), was obtained in analogy to example 3 from benzoimidazol-2-yl-methylamine, 2-(2-ethoxy-6-formyl-phenoxy)-3-methyl-butyric acid, and isocyano-cyclohexane.

EXAMPLE 132

7-Chloro-4-(2,6-difluoro-benzyl)-2-isopropyl-3-oxo-2,3,4,5-tetrahydro-benzo[f][1,4]oxazepine-5-carboxylic acid benzylamide The title compound, MS m/e: 499.2 (M+1), was obtained in analogy to example 3 from 2,6-difluorobenzylamine, 2-(4-chloro-2-formyl-phenoxy)-3-methyl-butyric acid, and isocyanomethyl-benzene.

EXAMPLE 133

7-Chloro-4-cyclohexyl-2-isopropyl-3-oxo-2,3,4,5-tetrahydro-benzo[f][1,4]oxazepine-5-carboxylic acid benzylamide The title compound, MS m/e: 455.3 (M+1), was obtained in analogy to example 3 from cyclohexylamine, 2-(4-chloro-2-formyl-phenoxy)-3-methyl-butyric acid, and isocyanomethyl-benzene.

EXAMPLE 134

{[7-Chloro-2-isopropyl-3-oxo-4-(3-trifluoromethyl-benzyl)-2,3,4,5-tetrahydro-benzo[f][1,4]oxazepine-5-carbonyl]-amino}-acetic acid tert-butyl ester The title compound, MS m/e: 577.18 (M+23), was obtained in analogy to example 3 from 3-trifluoromethyl-benzylamine, 2-(4-chloro-2-formyl-phenoxy)-3-methyl-butyric acid, and isocyano-acetic acid tert-butyl ester.

EXAMPLE 135

4-(1-Benzyl-piperidin-4-yl)-2-isopropyl-3-oxo-2,3,4,5-tetrahydro-benzo[f][1,4]oxazepine-5-carboxylic acid benzylamide The title compound, MS m/e: 512.4 (M+1), was obtained in analogy to example 3 from 1-benzyl-piperidin-4-ylamine, 2-(2-formyl-phenoxy)-3-methyl-butyric acid, and isocyanomethyl-benzene.

EXAMPLE 136

4-(1-Benzyl-piperidin-4-yl)-7-chloro-2-isopropyl-3-oxo-2,3,4,5-tetrahydro-benzo[f][1,4]oxazepine-5-carboxylic acid benzylamide The title compound, MS m/e: 546.3 (M+1), was obtained in analogy to example 3 from 1-benzyl-piperidin-4-ylamine, 2-(4-chloro-2-formyl-phenoxy)-3-methyl-butyric acid, and isocyanomethyl-benzene.

EXAMPLE 137

{[4-(1-Benzyl-piperidin-4-yl)-7-chloro-2-isopropyl-3-oxo-2,3,4,5-tetrahydro-benzo[f][1,4]oxazepine-5-carbonyl]-amino}-acetic acid tert-butyl ester The title compound, MS m/e: 570.3 (M+1), was obtained in analogy to example 3 from 1-benzyl-piperidin-4-ylamine, 2-(4-chloro-2-formyl-phenoxy)-3-methyl-butyric acid, and isocyano-acetic acid tert-butyl ester.

EXAMPLE 138

{[4-(1-Carbamoyl-2-phenyl-ethyl)-7-chloro-2-isopropyl-3-oxo-2,3,4,5-tetrahydro-benzo[f][1,4]oxazepine-5-carbonyl]-amino}-acetic acid tert-butyl ester The title compound, MS m/e: 566.21 (M+23), was obtained in analogy to example 3 from 2-amino-3-phenyl-propionamide, 2-(4-chloro-2-formyl-phenoxy)-3-methyl-butyric acid, and isocyano-acetic acid tert-butyl ester.

EXAMPLE 139

7-Chloro-4-[2-(1H-indol-3-yl)-ethyl]-2-isopropyl-3-oxo-2,3,4,5-tetrahydro-benzo[f][1,4]oxazepine-5-carboxylic acid benzylamide The title compound, MS m/e: 516.3 (M+1), was obtained in analogy to example 3 from 2-(1H-indol-3-yl)-ethylamine, 2-(4-chloro-2-formyl-phenoxy)-3-methyl-butyric acid, and isocyanomethyl-benzene.

EXAMPLE 140

7-Chloro-4-(4-dimethylamino-benzyl)-2-isopropyl-3-oxo-2,3,4,5-tetrahydro-benzo[f][1,4]oxazepine-5-carboxylic acid benzylamide The title compound, MS m/e: 528.3 (M+23), was obtained in analogy to example 3 from 4-dimethylaminobenzylamine, 2-(4-chloro-2-formyl-phenoxy)-3-methyl-butyric acid, and isocyanomethyl-benzene.

EXAMPLE 141

{[4-(2-Benzylsulfanyl-ethyl)-7-chloro-2-isopropyl-3-oxo-2,3,4,5-tetrahydro-benzo[f][1,4]oxazepine-5-carbonyl]-amino}-acetic acid tert-butyl ester The title compound, MS m/e: 569.3 (M+23), was obtained in analogy to example 3 from 2-benzylsulfanyl-ethylamine, 2-(4-chloro-2-formyl-phenoxy)-3-methyl-butyric acid, and isocyano-acetic acid tert-butyl ester.

EXAMPLE 142

{[7-Chloro-2-isopropyl-4-(2-methylsulfanyl-ethyl)-3-oxo-2,3,4,5-tetrahydro-benzo[f][1,4]oxazepine-5-carbonyl]-amino}-acetic acid tert-butyl ester The title compound, MS m/e: 493.3 (M+23), was obtained in analogy to example 3 from 2-methylsulfanyl-ethylamine, 2-(4-chloro-2-formyl-phenoxy)-3-methyl-butyric acid, and isocyano-acetic acid tert-butyl ester.

EXAMPLE 143

{[7-Chloro-2-isopropyl-3-oxo-4-(4-sulfamoyl-benzyl)-2,3,4,5-tetrahydro-benzo[f][1,4]oxazepine-5-carbonyl]-amino}-acetic acid tert-butyl ester The title compound, MS m/e: 588.3 (M+23), was obtained in analogy to example 3 from 4-aminomethyl-benzene-sulfonamide, 2-(4-chloro-2-formyl-phenoxy)-3-methyl-butyric acid, and isocyano-acetic acid tert-butyl ester.

EXAMPLE 144

({2-Isopropyl-4-[2-(5-nitro-pyridin-2-ylamino)-ethyl]-3-oxo-2,3,4,5-tetrahydro-benzo[f][1,4]oxazepine-5-carbonyl}-amino)-acetic acid tert-butyl ester The title compound, MS m/e: 528.3 (M+1), was obtained in analogy to example 3 from 2-(5-nitro-pyridin-2-ylamino)-ethylamine, 2-(2-formyl-phenoxy)-3-methyl-butyric acid, and isocyano-acetic acid tert-butyl ester.

EXAMPLE 145

4-(2,6-Difluoro-benzyl)-9-ethoxy-2-isopropyl-3-oxo-2,3,4,5-tetrahydro-benzo[f][1,4]oxazepine-5-carboxylic acid cyclohexylamide The title compound, MS m/e: 501.3 (M+1), was obtained in analogy to example 3 from 2,6-difluorobenzylamine, 2-(2-ethoxy-6-formyl-phenoxy)-3-methyl-butyric acid, and isocyano-cyclohexane.

EXAMPLE 146

4-(4-Dimethylamino-benzyl)-9-ethoxy-2-isopropyl-3-oxo-2,3,4,5-tetrahydro-benzo[f][1,4]oxazepine-5-carboxylic acid tert-butylamide The title compound, MS m/e: 482.4 (M+1), was obtained in analogy to example 3 from 4-dimethylaminobenzylamine, 2-(2-ethoxy-6-formyl-phenoxy)-3-methyl-butyric acid, and 2-isocyano-2-methyl-propane.

EXAMPLE 147

4-(1-Benzyl-piperidin-4-yl)-9-ethoxy-2-isopropyl-3-oxo-2,3,4,5-tetrahydro-benzo[f][1,4]oxazepine-5-carboxylic acid cyclohexylamide The title compound, MS m/e: 548.4 (M+1), was obtained in analogy to example 3 from 1-benzyl-piperidin-4-ylamine, 2-(2-ethoxy-6-formyl-phenoxy)-3-methyl-butyric acid, and isocyano-cyclohexane.

EXAMPLE 148

4-(4-Dimethylamino-benzyl)-9-ethoxy-2-isopropyl-3-oxo-2,3,4,5-tetrahydro-benzo[f][1,4]oxazepine-5-carboxylic acid cyclohexylamide The title compound, MS m/e: 529.4 (M+23), was obtained in analogy to example 3 from 4-dimethylaminobenzylamine, 2-(2-ethoxy-6-formyl-phenoxy)-3-methyl-butyric acid, and isocyano-cyclohexane.

EXAMPLE 149

9-Ethoxy-4-[2-(1H-indol-3-yl)-ethyl]-2-isopropyl-3-oxo-2,3,4,5-tetrahydro-benzo[f][1,4]oxazepine-5-carboxylic acid cyclohexylamide The title compound, MS m/e: 518.4 (M+1), was obtained in analogy to example 3 from 2-(1H-indol-3-yl)-ethylamine, 2-(2-ethoxy-6-formyl-phenoxy)-3-methyl-butyric acid, and isocyano-cyclohexane.

EXAMPLE 150

9-Ethoxy-2-isopropyl-4-[2-(5-methoxy-1H-indol-3-yl)-ethyl]-3-oxo-2,3,4,5-tetrahydro-benzo[f][1,4]oxazepine-5-carboxylic acid tert-butylamide The title compound, MS m/e: 522.4 (M+1), was obtained in analogy to example 3 from 2-(5-methoxy-1H-indol-3-yl)-ethylamine, 2-(2-ethoxy-6-formyl-phenoxy)-3-methyl-butyric acid, and 2-isocyano-2-methyl-propane.

EXAMPLE 151

9-Ethoxy-2-isopropyl-4-[2-(5-methoxy-1H-indol-3-yl)-ethyl]-3-oxo-2,3,4,5-tetrahydro-benzo[f][1,4]oxazepine-5-carboxylic acid cyclohexylamide The title compound, MS m/e: 548.4 (M+1), was obtained in analogy to example 3 from 2-(5-methoxy-1H-indol-3-yl)-ethylamine, 2-(2-ethoxy-6-formyl-phenoxy)-3-methyl-butyric acid, and isocyano-cyclohexane.

EXAMPLE 152

7-Bromo-4-(2-chloro-benzyl)-2-isopropyl-3-oxo-2,3,4,5-tetrahydro-benzo[f][1,4]oxazepine-5-carboxylic acid (2,6-dimethyl-phenyl)-amide The title compound, MS m/e: 555.2 (M+1), was obtained in analogy to example 3 from 2-chlorobenzylamine, 2-(4-bromo-2-formyl-phenoxy)-3-methyl-butyric acid, and 2-isocyano-1,3-dimethyl-benzene.

EXAMPLE 153

7-Bromo-4-cyclohexyl-2-isopropyl-3-oxo-2,3,4,5-tetrahydro-benzo[f][1,4]oxazepine-5-carboxylic acid (2,6-dimethyl-phenyl)-amide The title compound, MS m/e: 513.2 (M+1), was obtained in analogy to example 3 from cyclohexylamine, 2-(4-bromo-2-formyl-phenoxy)-3-methyl-butyric acid, and 2-isocyano-1,3-dimethyl-benzene.

EXAMPLE 154

7-Bromo-2-isopropyl-3-oxo-4-(2-thiophen-2-yl-ethyl)-2,3,4,5-tetrahydro-benzo[f][1,4]oxazepine-5-carboxylic acid (2,6-dimethyl-phenyl)-amide The title compound, MS m/e: 541.2 (M+1), was obtained in analogy to example 3 from 2-thiophen-2-yl-ethylamine, 2-(4-bromo-2-formyl-phenoxy)-3-methyl-butyric acid, and 2-isocyano-1,3-dimethyl-benzene.

EXAMPLE 155

4-(1-Benzyl-piperidin-4-yl)-7-bromo-2-isopropyl-3-oxo-2,3,4,5-tetrahydro-benzo[f][1,4]oxazepine-5-carboxylic acid (2,6-dimethyl-phenyl)-amide The title compound, MS m/e: 604.3 (M+1), was obtained in analogy to example 3 from 1-benzyl-piperidin-4-ylamine, 2-(4-bromo-2-formyl-phenoxy)-3-methyl-butyric acid, and 2-isocyano-1,3-dimethyl-benzene.

EXAMPLE 156

7-Bromo-2-isopropyl-3-oxo-4-pyridin-3-ylmethyl-2,3,4,5-tetrahydro-benzo[f][1,4]oxazepine-5-carboxylic acid (2,6-dimethyl-phenyl)-amide The title compound, MS m/e: 522.2 (M+1), was obtained in analogy to example 3 from pyridin-3-yl-methylamine, 2-(4-bromo-2-formyl-phenoxy)-3-methyl-butyric acid, and 2-isocyano-1,3-dimethyl-benzene.

EXAMPLE 157

7-Bromo-4-carbamoylmethyl-2-isopropyl-3-oxo-2,3,4,5-tetrahydro-benzo[f][1,4]oxazepine-5-carboxylic acid tert-butylamide The title compound, MS m/e: 440.2 (M+1), was obtained in analogy to example 3 from 2-amino-acetamide, 2-(4-bromo-2-formyl-phenoxy)-3-methyl-butyric acid, and 2-isocyano-2-methyl-propane.

EXAMPLE 158

7-Bromo-4-furan-2-ylmethyl-2-isopropyl-3-oxo-2,3,4,5-tetrahydro-benzo[f][1,4]oxazepine-5-carboxylic acid tert-butylamide The title compound, MS m/e: 485.1 (M+23), was obtained in analogy to example 3 from C-furan-2-yl-methylamine, 2-(4-bromo-2-formyl-phenoxy)-3-methyl-butyric acid, and 2-isocyano-2-methyl-propane.

EXAMPLE 159

7-Bromo-2-isopropyl-3-oxo-4-(2-phenyl-cyclopropyl)-2,3,4,5-tetrahydro-benzo[f][1,4]oxazepine-5-carboxylic acid cyclohexylamide The title compound, MS m/e: 525.2 (M+1), was obtained in analogy to example 3 from 2-phenyl-cyclopropylamine, 2-(4-bromo-2-formyl-phenoxy)-3-methyl-butyric acid, and isocyano-cyclohexane.

EXAMPLE 160

7-Bromo-4-(4-dimethylamino-benzyl)-2-isopropyl-3-oxo-2,3,4,5-tetrahydro-benzo[f][1,4]oxazepine-5-carboxylic acid tert-butylamide The title compound, MS m/e: 538.3 (M+23), was obtained in analogy to example 3 from 4-dimethylaminobenzylamine, 2-(4-bromo-2-formyl-phenoxy)-3-methyl-butyric acid, and 2-isocyano-2-methyl-propane.

EXAMPLE 161

7-Bromo-4-(4-dimethylamino-benzyl)-2-isopropyl-3-oxo-2,3,4,5-tetrahydro-benzo[f][1,4]oxazepine-5-carboxylic acid butylamide The title compound, MS m/e: 516.3 (M+1), was obtained in analogy to example 3 from 4-dimethylaminobenzylamine, 2-(4-bromo-2-formyl-phenoxy)-3-methyl-butyric acid, and 1-isocyano-butane.

EXAMPLE 162

4-(2-Benzylsulfanyl-ethyl)-7-bromo-2-isopropyl-3-oxo-2,3,4,5-tetrahydro-benzo[f][1,4]oxazepine-5-carboxylic acid cyclohexylamide The title compound, MS m/e: 559.2 (M+1), was obtained in analogy to example 3 from 2-benzylsulfanyl-ethylamine, 2-(4-bromo-2-formyl-phenoxy)-3-methyl-butyric acid, and isocyano-cyclohexane.

EXAMPLE 163

7-Bromo-2-isopropyl-4-(2-methylsulfanyl-ethyl)-3-oxo-2,3,4,5-tetrahydro-benzo[f][1,4]oxazepine-5-carboxylic acid cyclohexylamide The title compound, MS m/e: 483.2 (M+1), was obtained in analogy to example 3 from 2-methylsulfanyl-ethylamine, 2-(4-bromo-2-formyl-phenoxy)-3-methyl-butyric acid, and isocyano-cyclohexane.

EXAMPLE 164

7-Bromo-2-isopropyl-4-[2-(4-nitro-phenyl)-ethyl]-3-oxo-2,3,4,5-tetrahydro-benzo[f][1,4]oxazepine-5-carboxylic acid cyclohexylamide The title compound, MS m/e: 558.3 (M+1), was obtained in analogy to example 3 from 4-nitrophenylethylamine, 2-(4-bromo-2-formyl-phenoxy)-3-methyl-butyric acid, and isocyano-cyclohexane.

EXAMPLE 165

7-Bromo-4-(4-chloro-2-fluoro-benzyl)-2-isopropyl-3-oxo-2,3,4,5-tetrahydro-benzo[f][1,4]oxazepine-5-carboxylic acid cyclohexylamid The title compound, MS m/e: 551.2 (M+1), was obtained in analogy to example 3 from 4-chloro-2-fluorobenzylamine, 2-(4-bromo-2-formyl-phenoxy)-3-methyl-butyric acid, and isocyano-cyclohexane.

EXAMPLE 166

7-Bromo-4-(4-dimethylamino-benzyl)-2-isopropyl-3-oxo-2,3,4,5-tetrahydro-benzo[f][1,4]oxazepine-5-carboxylic acid cyclohexylamide The title compound, MS m/e: 564.3 (M+23), was obtained in analogy to example 3 from 4-dimethylaminobenzylamine, 2-(4-bromo-2-formyl-phenoxy)-3-methyl-butyric acid, and isocyano-cyclohexane.

EXAMPLE 167

7-Bromo-2-isopropyl-3-oxo-4-(2-oxo-tetrahydro-furan-3-yl)-2,3,4,5-tetrahydro-benzo[f][1,4]oxazepine-5-carboxylic acid cyclohexylamide The title compound, MS m/e: 493.2 (M+1), was obtained in analogy to example 3 from 3-amino-dihydro-furan-2-one, 2-(4-bromo-2-formyl-phenoxy)-3-methyl-butyric acid, and isocyano-cyclohexane.

EXAMPLE 168

7-Bromo-2-isopropyl-4-[2-(5-nitro-pyridin-2-ylamino)-ethyl]-3-oxo-2,3,4,5-tetrahydro-benzo[f][1,4]oxazepine-5-carboxylic acid cyclohexylamide The title compound, MS m/e: 574.2 (M+1), was obtained in analogy to example 3 from 2-(5-nitro-pyridin-2-ylamino)-ethylamine, 2-(4-bromo-2-formyl-phenoxy)-3-methyl-butyric acid, and isocyano-cyclohexane.

EXAMPLE 169

{[7-Bromo-4-(4-chloro-2-fluoro-benzyl)-2-isopropyl-9-methoxy-3-oxo-2,3,4,5-tetrahydro-benzo[f][1,4]oxazepine-5-carbonyl]-amino}-acetic acid tert-butyl ester The title compound, MS m/e: 635.1 (M+23), was obtained in analogy to example 3 from 4-chloro-2-fluorobenzylamine, 2-(4-bromo-2-formyl-6-methoxy-phenoxy)-3-methyl-butyric acid, and isocyano-acetic acid tert-butyl ester.

EXAMPLE 170

7-Bromo-2-isopropyl-9-methoxy-4-[2-(5-methoxy-1H-indol-3-yl)-ethyl]-3-oxo-2,3,4,5-tetrahydro-benzo[f][1,4]oxazepine-5-carboxylic acid (2,6-dimethyl-phenyl)-amide The title compound, MS m/e: 634.3 (M+1), was obtained in analogy to example 3 from 2-(5-methoxy-1H-indol-3-yl)-ethylamine, 2-(4-bromo-2-formyl-6-methoxy-phenoxy)-3-methyl-butyric acid, and 2-isocyano-1,3-dimethyl-benzene.

EXAMPLE 171

7-Bromo-2-isopropyl-9-methoxy-4-[2-(5-nitro-pyridin-2-ylamino)-ethyl]-3-oxo-2,3,4,5-tetrahydro-benzo[f][1,4]oxazepine-5-carboxylic acid (2,6-dimethyl-phenyl)-amide The title compound, MS m/e: 626.3 (M+1), was obtained in analogy to example 3 from 2-(5-nitro-pyridin-2-ylamino)-ethylamine, 2-(4-bromo-2-formyl-6-methoxy-phenoxy)-3-methyl-butyric acid, and 2-isocyano-1,3-dimethyl-benzene.

EXAMPLE 172

4-(4-Dimethylamino-benzyl)-2-isopropyl-8-methoxy-3-oxo-2,3,4,5-tetrahydro-benzo[f][1,4]oxazepine-5-carboxylic acid benzylamide The title compound, MS m/e: 502.4 (M+1), was obtained in analogy to example 3 from 4-dimethylaminobenzylamine, 2-(2-formyl-4-methoxy-phenoxy)-3-methyl-butyric acid, and isocyanomethyl-benzene.

EXAMPLE 173

4-(4-Dimethylamino-benzyl)-2-isopropyl-8-methoxy-3-oxo-2,3,4,5-tetrahydro-benzo[f][1,4]oxazepine-5-carboxylic acid (2,6-dimethyl-phenyl)-amide The title compound, MS m/e: 515.4 (M+1), was obtained in analogy to example 3 from 4-dimethylaminobenzylamine, 2-(2-formyl-4-methoxy-phenoxy)-3-methyl-butyric acid, and 2-isocyano-1,3-dimethyl-benzene.

EXAMPLE 174

2-tert-Butoxymethyl-7-chloro-4-(2,6-difluoro-benzyl)-3-oxo-2,3,4,5-tetrahydro-benzo[f][1,4]oxazepine-5-carboxylic acid cyclohexylamide The title compound, MS m/e: 557.21 (M+23), was obtained in analogy to example 3 from 2,6-difluorobenzylamine, 3-tert-butoxy-2-(4-chloro-2-formyl-phenoxy)-propionic acid, and isocyano-cyclohexane.

EXAMPLE 175

2-tert-Butoxymethyl-7-chloro-4-furan-2-ylmethyl-3-oxo-2,3,4,5-tetrahydro-benzo[f][1,4]oxazepine-5-carboxylic acid cyclohexylamide The title compound, MS m/e: 511.2 (M+23), was obtained in analogy to example 3 from furan-2-yl-methylamine, 3-tert-butoxy-2-(4-chloro-2-formyl-phenoxy)-propionic acid, and isocyano-cyclohexane.

EXAMPLE 176

7-Bromo-4-(2,6-difluoro-benzyl)-2-isopropyl-9-methoxy-3-oxo-2,3,4,5-tetrahydro-benzo[f][1,4]oxazepine-5-carboxylic acid cyclohexylamide The title compound, MS m/e: 565.2 (M+1), was obtained in analogy to example 3 from 2,6-difluorobenzylamine, 2-(4-bromo-2-formyl-6-methoxy-phenoxy)-3-methyl-butyric acid, and isocyano-cyclohexane.

EXAMPLE 177

4-(1-Benzyl-piperidin-4-yl)-7-bromo-2-isopropyl-9-methoxy-3-oxo-2,3,4,5-tetrahydro-benzo[f][1,4]oxazepine-5-carboxylic acid tert-butylamide The title compound, MS m/e: 586.3 (M+1), was obtained in analogy to example 3 from 1-benzyl-piperidin-4-ylamine, 2-(4-bromo-2-formyl-6-methoxy-phenoxy)-3-methyl-butyric acid, and 2-isocyano-2-methyl-propane.

EXAMPLE 178

7-Bromo-4-(4-dimethylamino-benzyl)-2-isopropyl-9-methoxy-3-oxo-2,3,4,5-tetrahydro-benzo[f][1,4]oxazepine-5-carboxylic acid cyclohexylamide The title compound, MS m/e: 594.3 (M+23), was obtained in analogy to example 3 from 4-dimethylaminobenzylamine, 2-(4-bromo-2-formyl-6-methoxy-phenoxy)-3-methyl-butyric acid, and isocyano-cyclohexane.

EXAMPLE 179

4-(1-Benzyl-piperidin-4-yl)-7-bromo-2-isopropyl-9-methoxy-3-oxo-2,3,4,5-tetrahydro-benzo[f][1,4]oxazepine-5-carboxylic acid butylamide The title compound, MS m/e: 586.3 (M+1), was obtained in analogy to example 3 from 1-benzyl-piperidin-4-ylamine, 2-(4-bromo-2-formyl-6-methoxy-phenoxy)-3-methyl-butyric acid, and 1-isocyano-butane.

EXAMPLE 180

7-Bromo-4-(4-dimethylamino-benzyl)-2-isopropyl-9-methoxy-3-oxo-2,3,4,5-tetrahydro-benzo[f][1,4]oxazepine-5-carboxylic acid butylamide The title compound, MS m/e: 568.3 (M+23), was obtained in analogy to example 3 from 4-dimethylaminobenzylamine, 2-(4-bromo-2-formyl-6-methoxy-phenoxy)-3-methyl-butyric acid, and 1-isocyano-butane.

EXAMPLE 181

7-Bromo-2-isopropyl-9-methoxy-3-oxo-4-pyridin-3-ylmethyl-2,3,4,5-tetrahydro-benzo[f][1,4]oxazepine-5-carboxylic acid cyclohexylamide The title compound, MS m/e: 530.3 (M+1), was obtained in analogy to example 3 from pyridin-3-yl-methylamine, 2-(4-bromo-2-formyl-6-methoxy-phenoxy)-3-methyl-butyric acid, and isocyano-cyclohexane.

EXAMPLE 182

7-Bromo-4-[2-(1H-indol-3-yl)-ethyl]-2-isopropyl-9-methoxy-3-oxo-2,3,4,5tetrahydro-benzo[f][1,4]oxazepine-5-carboxylic acid tert-butylamide The title compound, MS m/e: 556.3 (M+1), was obtained in analogy to example 3 from 2-(1H-indol-3-yl)-ethylamine, 2-(4-bromo-2-formyl-6-methoxy-phenoxy)-3-methyl-butyric acid, and 2-isocyano-2-methyl-propane.

EXAMPLE 183

7-Bromo-2-is6propyl-9-methoxy-4-[2-(5-methoxy-1H-indol-3-yl)-ethyl]-3-oxo-2,3,4,5-tetrahydro-benzo[f][1,4]oxazepine-5-carboxylic acid tert-butylamide The title compound, MS m/e: 586.3 (M+1), was obtained in analogy to example 3 from 2-(5-methoxy-1H-indol-3-yl)-ethylamine, 2-(4-bromo-2-formyl-6-methoxy-phenoxy)-3-methyl-butyric acid, and 2-isocyano-2-methyl-propane.

EXAMPLE 184

7-Bromo-2-isopropyl-9-methoxy-4-[2-(5-methoxy-1H-indol-3-yl)-ethyl]-3-oxo-2,3,4,5-tetrahydro-benzo[f][1,4]oxazepine-5-carboxylic acid cyclohexylamide The title compound, MS m/e: 612.3 (M+1), was obtained in analogy to example 3 from 2-(5-methoxy-1H-indol-3-yl)-ethylamine, 2-(4-bromo-2-formyl-6-methoxy-phenoxy)-3-methyl-butyric acid, and isocyano-cyclohexane.

EXAMPLE 185

7-Bromo-2-isopropyl-9-methoxy-4-[2-(5-nitro-pyridin-2-ylamino)-ethyl]-3-oxo-2,3,4,5-tetrahydro-benzo[f][1,4]oxazepine-5-carboxylic acid cyclohexylamide The title compound, MS m/e: 604.3 (M+1), was obtained in analogy to example 3 from 2-(5-nitro-pyridin-2-ylamino)-ethylamine, 2-(4-bromo-2-formyl-6-methoxy-phenoxy)-3-methyl-butyric acid, and isocyano-cyclohexane.

EXAMPLE 186

{[7-Bromo-4-(2-chloro-benzyl)-2-isopropyl-9-methoxy-3-oxo-2,3,4,5-tetrahydro-benzo[f][1,4]oxazepine-5-carbonyl]-amino}-acetic acid tert-butyl ester The title compound, MS m/e: 617.2 (M+23), was obtained in analogy to example 3 from 2-chlorobenzylamine, 2-(4-bromo-2-formyl-6-methoxy-phenoxy)-3-methyl-butyric acid, and isocyano-acetic acid tert-butyl ester.

EXAMPLE 187

[(7-Bromo-4-carbamoylmethyl-2-isopropyl-9-methoxy-3-oxo-2,3,4,5-tetrahydro-benzo[f][1,4]oxazepine-5-carbonyl)-amino]-acetic acid tert-butyl ester The title compound, MS m/e: 550.2 (M+23), was obtained in analogy to example 3 from 2-amino-acetamide, 2-(4-bromo-2-formyl-6-methoxy-phenoxy)-3-methyl-butyric acid, and isocyano-acetic acid tert-butyl ester.

EXAMPLE 188

{[7-Bromo-4-(3,5-dichloro-benzyl)-2-isopropyl-9-methoxy-3-oxo-2,3,4,5-tetrahydro-benzo[f][1,4]oxazepine-5-carbonyl]-amino}-acetic acid tert-butyl ester The title compound, MS m/e: 651.07 (M+23), was obtained in analogy to example 3 from 3,5-dichlorobenzylamine, 2-(4-bromo-2-formyl-6-methoxy-phenoxy)-3-methyl-butyric acid, and isocyano-acetic acid tert-butyl ester.

EXAMPLE 189

{[7-Bromo-2-isopropyl-9-methoxy-3-oxo-4-(2-phenyl-cyclopropyl)-2,3,4,5-tetrahydro-benzo[f][1,4]oxazepine-5-carbonyl]-amino}-acetic acid tert-butyl ester The title compound, MS m/e: 587.2 (M+1), was obtained in analogy to example 3 from 2-phenyl-cyclopropylamine, 2-(4-bromo-2-formyl-6-methoxy-phenoxy)-3-methyl-butyric acid, and isocyano-acetic acid tert-butyl ester.

EXAMPLE 190

{[7-Bromo-2-isopropyl-9-methoxy-3-oxo-4-(1,2,3,4-tetrahydro-naphthalen-1-yl)-2,3,4,5-tetrahydro-benzo[f][1,4]oxazepine-5-carbonyl]-amino}-acetic acid tert-butyl ester The title compound, MS m/e: 623.3 (M+23), was obtained in analogy to example 3 from 1,2,3,4-tetrahydro-naphthalen-1-ylamine, 2-(4-bromo-2-formyl-6-methoxy-phenoxy)-3-methyl-butyric acid, and isocyano-acetic acid tert-butyl ester.

EXAMPLE 191

[(7-Bromo-2-isopropyl-9-methoxy-3-oxo-4-pyridin-3-ylmethyl-2,3,4,5-tetrahydro-benzo[f][1,4]oxazepine-5-carbonyl)-amino]-acetic acid tert-butyl ester The title compound, MS m/e: 562.2 (M+1), was obtained in analogy to example 3 from pyridin-3-yl-methylamine, 2-(4-bromo-2-formyl-6-methoxy-phenoxy)-3-methyl-butyric acid, and isocyano-acetic acid tert-butyl ester.

EXAMPLE 192

[(4-Benzo[1,3]dioxol-5-ylmethyl-7-bromo-2-isopropyl-9-methoxy-3-oxo-2,3,4,5-tetrahydro-benzo[f][1,4]oxazepine-5-carbonyl)-amino]-acetic acid tert-butyl ester The title compound, MS m/e: 627.3 (M+23), was obtained in analogy to example 3 from benzo[1,3]dioxol-5-yl-methylamine, 2-(4-bromo-2-formyl-6-methoxy-phenoxy)-3-methyl-butyric acid, and isocyano-acetic acid tert-butyl ester.

EXAMPLE 193

9-Ethoxy-4-[2-(1H-indol-3-yl)-ethyl]-2-isopropyl-3-oxo-2,3,4,5-tetrahydro-benzo[f][1,4]oxazepine-5-carboxylic acid (2,6-dimethyl-phenyl)-amide The title compound, MS m/e: 540.4 (M+1), was obtained in analogy to example 3 from 2-(1H-indol-3-yl)-ethylamine, 2-(2-ethoxy-6-formyl-phenoxy)-3-methyl-butyric acid, and 2-isocyano-1,3-dimethyl-benzene.

EXAMPLE 194

8-Diethylamino-2-isopropyl-4-(1-naphthalen-1-yl-ethyl)-3-oxo-2,3,4,5-tetrahydro-benzo[f][1,4]oxazepine-5-carboxylic acid benzylamide The title compound, MS m/e: 564.4 (M+1), was obtained in analogy to example 3 from 1-naphthalen-1-yl-ethylamine, 2-(5-diethylamino-2-formyl-phenoxy)-3-methyl-butyric acid, and isocyanomethyl-benzene.

EXAMPLE 195

8-Diethylamino-4-furan-2-ylmethyl-2-isopropyl-3-oxo-2,3,4,5-tetrahydro-benzo[f][1,4]oxazepine-5-carboxylic acid benzylamide The title compound, MS m/e: 490.4 (M+1), was obtained in analogy to example 3 from C-furan-2-yl-methylamine, 2-(5-diethylamino-2-formyl-phenoxy)-3-methyl-butyric acid, and isocyanomethyl-benzene.

EXAMPLE 196

2-Isopropyl-8-methoxy-4-(1-naphthalen-1-yl-ethyl)-3-oxo-2,3,4,5-tetrahydro-benzo[f][1,4]oxazepine-5-carboxylic acid (2,6-dimethyl-phenyl)-amide The title compound, MS m/e: 559.3 (M+23), was obtained in analogy to example 3 from 1-naphthalen-1-yl-ethylamine, 2-(2-formyl-5-methoxy-phenoxy)-3-methyl-butyric acid, and 2-isocyano-1,3-dimethyl-benzene.

| Tablet Formulation (Wet Granulation) | | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | mg/capsule | | | |
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| | Talc | 10 | 15 | 10 | 25 |
| | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula

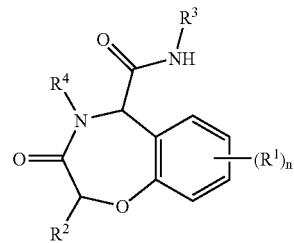

I wherein
$R^1$ is, lower alkoxy, halogen or —NR'R";
n is 1 or 2;
R' and R" are each independently hydrogen or lower alkyl;
$R^2$ is hydrogen, lower alkyl, —$(CH_2)_m$-cycloalkyl, —$(CH_2)_m$-phenyl or —$(CH_2)_m$—O-lower alkyl;
m is 0, 1 or 2;
$R^3$ is lower alkyl, —$(CH_2)_m$—C(O)O-lower alkyl, cycloalkyl or —$(CH_2)_m$-phenyl, which is unsubstituted or substituted by one or two substituents, selected from the group consisting of halogen or lower alkyl;

$R^4$ is —$(CH_2)_o$-phenyl, which is unsubstituted or substituted by one or two substituents selected from the group consisting of halogen, trifluoromethyl, —NR'R", nitro and
—$SO_2NH_2$, or is
-cycloalkyl, unsubstituted or substituted by phenyl, or is
—$(CR'R'')_o$-heterocyclyl, selected from the group consisting of
tetrahydropyran-4-yl,
pyridin-3-yl,
indol-3-yl optionally substituted by halogen or lower alkoxy,
thiophen-2-yl,
furan-2-yl,
benzoimidazol-2-yl,
2-oxo-tetrahydrofuran, and
benzo[1,3]dioxol-5-yl or is
—NH-pyridin-2-yl optionally substituted by nitro,
1-benzyl-piperidin-4-yl,
-tetrahydro-naphthalen-1-yl,
—CHR'-naphthalen-2-yl,
-fluoren-9-yl,
—$(CH_2)_o$—S-lower alkyl,
—$(CH_2)_o$—S-benzyl,
—$(CH_2)_o$—C(O)NH_2,
—$(CH_2)_o$NR'R",
—CH[C(O)NH_2]—$(CH_2)_o$-phenyl,
—$(CH_2)_o$—CF_3, or
—$(CH_2)_o$—CR'R"—CH_2—NR'R";
and o is 1 or 2;
or a pharmaceutically suitable acid addition salt thereof.

2. A compound of claim 1, wherein $R^2$ is lower alkyl.

3. A compound of claim 2, wherein $R^3$ is cycloalkyl.

4. A compound of claim 3, wherein $R^4$ is —$(CH_2)_o$-phenyl, substituted by
di-halogen or NR'R".

5. A compound of claim 4, which is
7-bromo-4-(2,6-difluoro-benzyl)-2-isopropyl-3-oxo-2,3,4,5-tetrahydro-benzo[f][1,4]oxazepine-5-carboxylic acid cyclohexylamide,
7-chloro-4-(4-chloro-2-fluoro-benzyl)-2-isopropyl-3-oxo-2,3,4,5-tetrahydro-benzo[f][1,4]oxazepine-5-carboxylic acid cyclohexylamide,
7-bromo-4-(4-chloro-2-fluoro-benzyl)-2-isopropyl-3-oxo-2,3,4,5-tetrahydro-benzo[f][1,4]oxazepine-5-carboxylic acid cyclohexylamide or
7-bromo-4-(4-dimethylamino-benzyl)-2-isopropyl-9-methoxy-3-oxo-2,3,4,5-tetrahydro-benzo[f][1,4]oxazepine-5-carboxylic acid cyclohexylamide.

6. A compound of claim 3, wherein $R^4$ is tetrahydropyran-4-yl.

7. A compound of claim 6, which is
7-chloro-2-ethyl-3-oxo-4-(tetrahydro-pyran-4-yl)-2,3,4,5-tetrahydro-benzo[f][1,4]oxazepine-5-carboxylic acid cyclohexylamide.

8. A compound of claim 3, wherein $R^4$ is tetrahydronaphthalen-1-yl.

9. A compound of claim 8, which is
7-chloro-2-isopropyl-3-oxo-4-(1,2,3,4-tetrahydro-naphthalen-1-yl)-2,3,4,5-tetrahydro-benzo[f][1,4]oxazepine-5-carboxylic acid cyclohexylamide or
8-diethylamino-2-isopropyl-3-oxo-4-(1,2,3,4-tetrahydro-naphthalen-1-yl)-2,4,3,4,5-tetrahydro-benzo[f][1,4]oxazepine-5-carboxylic acid cyclohexylamide.

10. A compound of claim 3, wherein $R^4$ is —$(CH_2)_o$-pyridin-3-yl.

11. A compound of claim 10, which is
7-chloro-2-isopropyl-3-oxo-4-pyridin-3-ylmethyl-2,3,4,5-tetrahydro-benzo[f][1,4]oxazepine-5-carboxylic acid cyclohexylamide.

12. A compound of claim 2, wherein $R^3$ is lower alkyl.

13. A compound of claim 12, wherein $R^4$ is —$(CH_2)_o$-phenyl, substituted by
di-halogen or NR'R".

14. A compound of claim 13, which is
7-chloro-4-(2,6-difluoro-benzyl)-2-ethyl-3-oxo-2,3,4,5-tetrahydro-benzo[f][1,4]oxazepine-5-carboxylic acid tert-butylamide,
7-chloro-4-(4-dimethylamino-benzyl)-2-isopropyl-3-oxo-2,3,4,5-tetrahydro-benzo[f][1,4]oxazepine-5-carboxylic acid butylamide, 4-(4-dimethylamino-benzyl)-2-isopropyl-8-methoxy-3-oxo-2,3,4,5-tetrahydro-benzo[f][1,4]oxazepine-5-carboxylic acid butylamide or
7-bromo-4-(4-dimethylamino-benzyl)-2-isopropyl-3-oxo-2,3,4,5-tetrahydro-benzo[f][1,4]oxazepine-5-carboxylic acid tert-butylamide.

15. A compound of claim 12, wherein $R^4$ is —$(CR'R'')_o$-indol-3-yl, substituted by lower alkoxy.

16. A compound of claim 15, which is 9-ethoxy-2-isopropyl-4-[2-(5-methoxy-1H-indol-3-yl)-ethyl]-3-oxo-2,3,4,5-tetrahydro-benzo[f][1,4]oxazepine-5-carboxylic acid tert-butylamide.

17. A compound of claim 12, wherein $R^4$ is cycloalkyl.

18. A compound of claim 17, which is
7-chloro-4-cyclopentyl-2-ethyl-3-oxo-2,3,4,5-tetrahydro-benzo[f][1,4]oxazepine-5-carboxylic acid tert-butylamide.

19. A compound of claim 12, wherein $R^4$ is —$(CH_2)_o$-benzo[1,3]dioxol-5-yl.

20. A compound of claim 19, which is 4-benzo[1,3]dioxol-5-ylmethyl-8-diethylamino-2-isopropyl-3-oxo-2,3,4,5-tetrahydro-benzo[f][1,4]oxazepine-5-carboxylic acid tert-butylamide.

21. A compound of claim 12, wherein $R^4$ is 1-benzyl-piperidin-4-yl.

22. A compound of claim 2, wherein $R^3$ is —$(CH_2)_m$-phenyl.

23. A compound of claim 22, wherein $R^4$ is cycloalkyl.

24. A compound of claim 23, which is
7-chloro-4-cyclohexyl-2-isopropyl-3-oxo-2,3,4,5-tetrahydro-benzo[f][1,4]oxazepine-5-carboxylic acid benzylamide.

25. A compound of claim 2, wherein $R^3$ is —$(CH_2)_m$—C(O)O-lower alkyl.

26. A compound of claim 25, wherein $R^4$ is —$(CH_2)_o$-phenyl, substituted by $CF_3$ or halogen.

27. A compound of claim 26, which is
{[7-chloro-2-isopropyl-3-oxo-4-(3-trifluoromethyl-benzyl)-2,3,4,5-tetrahydro-benzo[f][1,4]oxazepine-5-carbonyl]-amino}-acetic acid tert-butyl ester or
{[7-bromo-4-(2-chloro-benzyl)-2-isopropyl-9-methoxy-3-oxo-2,3,4,5-tetrahydro-benzo[f][1,4]oxazepine-5-carbonyl]-amino}-acetic acid tert-butyl ester.

28. A compound of claim 1, wherein $R^3$ is lower alkyl or cycloalkyl.

29. A compound of claim 1, wherein $R^3$ is —$(CH_2)_m$-phenyl which is unsubstituted or substituted by one or two substituents selected from the group consisting of halogen or lower alkyl.

30. A compound of claim 1, wherein $R^3$ is —$(CH_2)_m$—C(O)O-lower alkyl.

31. A compound of claim 1, wherein $R^4$ is —$(CH_2)_o$-phenyl which is unsubstituted or substituted by one or two substituents selected from the group consisting of halogen, trifluoromethyl, NR'R", nitro or $SO_2NH_2$.

32. A compound of claim 1, wherein $R^4$ is cycloalkyl which is unsubstituted or substituted by phenyl.

33. A compound of claim 1, wherein $R^4$ is CR'R"heterocycle selected from the group consisting of
tetrahydropyran-4-yl,
pyridin-3-yl,
indol-3-yl optionally substituted by halogen or lower alkoxy,
thiophen-2-yl,
furan-2-yl,
benzoimidazol-2-yl,
2-oxo-tetrahydrofuran, and
benzo[1,3]dioxol-5-yl or is
—NH-pyridin-2-yl optionally substituted by nitro, or
1-benzyl-piperidin-4-yl.

34. A composition comprising a compound of formula

I wherein
$R^1$ is, lower alkoxy, halogen or —NR'R";
n is 1 or 2;
R' and R" are each independently hydrogen or lower alkyl;
$R^2$ is hydrogen, lower alkyl, —$(CH_2)_m$-cycloalkyl, —$(CH_2)_m$-phenyl or
—$(CH_2)_m$—O-lower alkyl;
m is 0, 1 or 2;
$R^3$ is lower alkyl, —$(CH_2)_m$—C(O)O-lower alkyl, cycloalkyl or $(CH_2)_m$-phenyl, which is unsubstituted or substituted by one or two substituents, selected from the group consisting of halogen or lower alkyl;
$R^4$ is —$(CH_2)_o$-phenyl, which is unsubstituted or substituted by one or two substituents selected from the group consisting of halogen, trifluoromethyl, —NR'R", nitro and
—$SO_2NH_2$, or is
-cycloalkyl, unsubstituted or substituted by phenyl, or is
—$(CR'R")_o$-heterocyclyl, selected from the group consisting of
tetrahydropyran-4-yl,
pyridin-3-yl,
indol-3-yl optionally substituted by halogen or lower alkoxy,
thiophen-2-yl,
furan-2-yl,
benzoimidazol-2-yl,
2-oxo-tetrahydrofuran,
benzo[1,3]dioxol-5-yl or is
—NH-pyridin-2-yl optionally substituted by nitro,
1-benzyl-piperidin-4-yl,
-tetrahydro-naphthalen-1-yl,
—CHR'-naphthalen-2-yl,
-fluoren-9-yl,
—$(CH_2)_o$—S-lower alkyl,
—$(CH_2)_o$—S-benzyl,
—$(CH_2)_o$—C(O)NH_2,
—$(CH_2)_o$NR'R",
—CH[C(O)NH_2]—$(CH_2)_o$-phenyl,
—$(CH_2)_o$—CF_3, or
—$(CH_2)_o$—CR'R"—CH_2—NR'R";
and o is 1 or 2;
or a pharmaceutically suitable acid addition salt thereof and a pharmaceutically acceptable carrier.

35. A process for preparing a compound of formula I

I wherein
$R^1$ is, lower alkoxy, halogen or —NR'R";
n is 1 or 2;
R' and R" are each independently hydrogen or lower alkyl;
$R^2$ is hydrogen, lower alkyl, —$(CH_2)_m$-cycloalkyl, —$(CH_2)_m$-phenyl or
—$(CH_2)_m$—O-lower alkyl;
m is 0, 1 or 2;
$R^3$ is lower alkyl, —$(CH_2)_m$—C(O)O-lower alkyl, cycloalkyl or $(CH_2)_m$-phenyl, which is unsubstituted or substituted by one or two substituents, selected from the group consisting of halogen or lower alkyl;
$R^4$ is —$(CH_2)_o$-phenyl, which is unsubstituted or substituted by one or two substituents selected from the group consisting of halogen, trifluoromethyl, —NR'R", nitro and
—$SO_2NH_2$, or is
-cycloalkyl, unsubstituted or substituted by phenyl, or is
—$(CR'R")_o$-heterocyclyl, selected from the group consisting of
tetrahydropyran-4-yl,
pyridin-3-yl,
indol-3-yl optionally substituted by halogen or lower alkoxy,
thiophen-2-yl,
furan-2-yl,
benzoimidazol-2-yl,
2-oxo-tetrahydrofuran, and
benzo[1,3]dioxol-5-yl or is
—NH-pyridin-2-yl optionally substituted by nitro,
1-benzyl-piperidin-4-yl,
-tetrahydro-naphthalen-1-yl,
—CHR'-naphthalen-2-yl,
-fluoren-9-yl,
—$(CH_2)_o$—S-lower alkyl,
—$(CH_2)_o$—S-benzyl,
—$(CH_2)_o$—C(O)NH_2,
—$(CH_2)_o$NR'R",
—CH[C(O)NH_2]—$(CH_2)_o$-phenyl,
—$(CH_2)_o$—CF_3, or
—$(CH_2)_o$—CR'R"—CH_2—NR'R";

and o is 1 or 2;
or a pharmaceutically suitable acid addition salt thereof
which process comprises
a) reacting a compound of formula

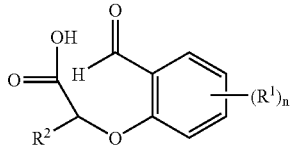

II with a compound of formula

    III and with a compound of formula

    IV to a produce compound of formula    I

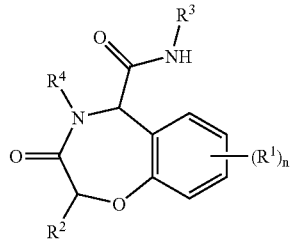

wherein the substituents are as defined above.

36. A compound of formula    I

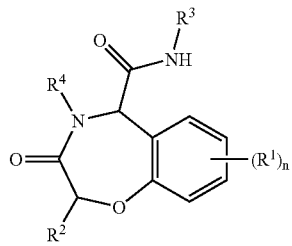

wherein
$R^1$ is hydrogen, lower alkoxy, halogen or —NR'R";
n is 1 or 2;
R' and R" are each independently hydrogen or lower alkyl;

$R^2$ is hydrogen, lower alkyl, —$(CH_2)_m$-cycloalkyl, —$(CH_2)_m$-phenyl or
—$(CH_2)_m$—O-lower alkyl;
m is 0, 1 or 2;
R is lower alkyl, —$(CH_2)_m$—C(O)O-lower alkyl, cycloalkyl, or —$(CH_2)_m$-phenyl, which is unsubstituted or substituted by one or two substituents, selected from the group consisting of halogen or lower alkyl;
$R^4$ is —$(CH_2)_o$-phenyl, which is substituted by one or two substituents selected from the group consisting of halogen, trifluoromethyl, —NR'R", nitro and
—$SO_2NH_2$, or is
-cycloalkyl substituted by phenyl, or is
—$(CR'R")_o$-heterocyclyl, selected from the group consisting of tetrahydropyran-4-yl,
pyridin-3-yl,
indol-3-yl optionally substituted by halogen or lower alkoxy;
thiophen-2-yl,
furan-2-yl,
benzoimidazol-2-yl,
2-oxo-tetrahydrofuran,
benzo[1,3]dioxol-5-yl or is
—NH-pyridin-2-yl optionally substituted by nitro,
1-benzyl-piperidin-4-yl,
-tetrahydro-naphthalen-1-yl,
—CHR'-naphthalen-2-yl,
-fluoren-9-yl,
—$(CH_2)_o$—S-lower alkyl,
—$(CH_2)_o$—S-benzyl,
—$(CH_2)_o$—C(O)$NH_2$,
—$(CH_2)_o$NR'R",
—CH[C(O)$NH_2$]—$(CH_2)_o$-phenyl,
—$(CH_2)_o$—$CF_3$, or
—$(CH_2)_o$—CR'R"—$CH_2$—NR'R";
and o is 1 or 2;
or a pharmaceutically suitable acid addition salt thereof.

37. A compound of claim 36, selected from the group consisting of
4-(4-dimethylamino-benzyl)-2-isopropyl-3-oxo-2,3,4,5-tetrahydro-benzo[f][1,4]oxazepine-5-carboxylic acid butylamide, and
4-(1-benzyl-piperidin-4-yl)-2-isopropyl-3-oxo-2,3,4,5-tetrahydro-benzo[f][1,4]oxazepine-5-carboxylic acid tert-butylamide.

* * * * *

UNITED STATES PATENT AND TRADEMARK OFFICE
CERTIFICATE OF CORRECTION

PATENT NO. : 7,060,698 B2  Page 1 of 1
APPLICATION NO. : 10/838054
DATED : June 13, 2006
INVENTOR(S) : Galley et al.

It is certified that error appears in the above-identified patent and that said Letters Patent is hereby corrected as shown below:

IN THE CLAIMS:

Claim 9, Column 45, line 66: "naphthalen-1-yl)-2,4,3,4,5-tetrahydro-benzo-[f][1,4]" should read -- naphthalen-1-yl)-2,3,4,5,tetrahydro-benzo-[f][1,4] -- .

Claim 36, Column 50, line 5: "R is lower alkyl," should read -- $R^3$ is lower alkyl, -- .

Signed and Sealed this

Second Day of January, 2007

JON W. DUDAS
*Director of the United States Patent and Trademark Office*